United States Patent
Zhu

(10) Patent No.: US 10,858,711 B2
(45) Date of Patent: Dec. 8, 2020

(54) PRIMERS, PROBES AND METHODS FOR SENSITIVE, SPECIFIC DETECTION AND MONITORING OF HIV-1 AND HCV

(71) Applicant: UNIVERSITY OF WASHINGTON, Seattle, WA (US)

(72) Inventor: Tuofu Zhu, Seattle, WA (US)

(73) Assignee: UNIVERSITY OF WASHINGTON, Seattle, WA (US)

(*) Notice: Subject to any disclaimer, the term of this patent is extended or adjusted under 35 U.S.C. 154(b) by 207 days.

(21) Appl. No.: 15/553,083

(22) PCT Filed: Feb. 23, 2016

(86) PCT No.: PCT/US2016/019101
§ 371 (c)(1),
(2) Date: Aug. 23, 2017

(87) PCT Pub. No.: WO2016/137975
PCT Pub. Date: Sep. 1, 2016

(65) Prior Publication Data
US 2018/0037961 A1 Feb. 8, 2018

Related U.S. Application Data

(60) Provisional application No. 62/119,672, filed on Feb. 23, 2015.

(51) Int. Cl.
*C12Q 1/68* (2018.01)
*C12Q 1/70* (2006.01)

(52) U.S. Cl.
CPC ............ *C12Q 1/703* (2013.01); *C12Q 1/707* (2013.01)

(58) Field of Classification Search
None
See application file for complete search history.

(56) References Cited

U.S. PATENT DOCUMENTS

| | | | |
|---|---|---|---|
| 6,001,558 A | 12/1999 | Backus et al. | |
| 6,623,919 B1 | 9/2003 | Gorman et al. | |
| 10,196,684 B2 * | 2/2019 | Ismagilov | C12Q 1/6844 |
| 2006/0172325 A1 | 8/2006 | Brownstein et al. | |
| 2010/0099162 A1 | 4/2010 | Muesing et al. | |
| 2011/0105593 A1 | 5/2011 | Steel et al. | |
| 2011/0214205 A1 | 9/2011 | Dietrich et al. | |
| 2012/0035240 A1 | 2/2012 | Pachuck et al. | |

OTHER PUBLICATIONS

Fishman et al. (Journal of Infectious Disease, 2008, 197:597-607) (Year: 2008).*
Bostan et al. (Genbank entry GU324081, Dec. 2012) (Year: 2012).*
Lowe et al. (Nucleic Acids Research, 1990, 18(7):1757-1761) (Year: 1990).*
Farma et al. (Journal of Clin Microbiol, 1996, 34(12):3171-3174) (Year: 1996).*
International Search Report for PCT/US16/19101 (WO2016137975 Published Sep. 1, 2016).
Palmer, Sarah, et al. New Real-Time Reverse Transcriptase-Initiated PCR Assay with Single-Copy Sensitivity for Human Immunodeficiency Virus Type 1 RNA in Plasma. Journal of Clinical Microbiology, Oct. 2003, vol. 41, No. 10. p. 4531-4536.
Aitken et al., Development and evaluation of an affordable real-time qualitative assay for determining HIV-1 virological failure in plasma and dried blood spots, J. Clin. Microbiol. Jun. 2013 ; 51:6 1899-1905.
Alter, M.J., et al., The prevalence of hepatitis C virus infection in the United States, 1988 through 1994. N Engl J Med, 1999. 341(8): p. 556-62.
Archin, N.M., et al., Administration of vorinostat disrupts HIV-1 latency in patients on antiretroviral therapy. Nature, 2012. 487(7408): p. 482-5.
Centers for Disease Control and Prevention. Recommendations for prevention and control of hepatitis C virus (HCV) infection and HCV-related chronic disease. MMWR 1998;47(No. RR-19):p. 1-39.
Chun, T.W., et al., In vivo fate of HIV-1-infected T cells: Quantitative analysis of the transition to stable latency. Nature Med., 1995. 1(12): p. 1284-1290.
Chun, T.W., et al., Presence of an inducible HIV-1 latent reservoir during highly active antiretroviral therapy. Proc. Natl. Acad. Sci. USA, 1997. 94(24): p. 13193-7.
Chun, T.W., et al., Quantification of latent tissue reservoirs and total body viral load in HIV-1 infection. Nature, 1997. 387(6629): p. 183-8.
Chun, T.W., et al., Relationship between pre-existing viral reservoirs and the reemergence of plasma viremia after discontinuation of highly active anti-retroviral therapy [see comments]. Nat Med, 2000. 6(7): p. 757-61.
Davey, R.T., Jr., et al., HIV-1 and T cell dynamics after interruption of highly active antiretroviral therapy (HAART) in patients with a history of sustained viral suppression. Proc Natl Acad Sci U S A, 1999. 96(26): p. 15109-14.
Deeks, S.G., et al., Towards an HIV cure: a global scientific strategy. Nat Rev Immunol, 2012. 12(8): p. 607-14.
Dinoso, J.B., et al., A comparison of viral loads between HIV-1-infected elite suppressors and individuals who receive suppressive highly active antiretroviral therapy. Clin Infect Dis, 2008.47(1): p. 102-4.
Dinoso, J.B., et al., Treatment intensification does not reduce residual HIV-1 viremia in patients on highly active antiretroviral therapy. Proc Natl Acad Sci U S A, 2009. 106(23): p. 9403-8.

(Continued)

*Primary Examiner* — Stephanie K Mummert
(74) *Attorney, Agent, or Firm* — Karen S Canady; canady + lortz LLP

(57) ABSTRACT

Primers and probes for detecting an RNA virus, including HIV, HIV-1 subtypes of the M and O groups, and HCV, in a sample. The primers and probes can be used for monitoring the efficacy of anti-retroviral treatment in a subject infected with HIV and/or HCV, and for detecting acute HIV-1 infection, and/or acute HCV infection, in a subject. Included are inner, middle and outer primers that can be used in PCR, including triple nested PCR in a single tube. The methods are highly sensitive and specific, allowing for detection of as few as 4 copies of virus in a sample.

25 Claims, 12 Drawing Sheets
Specification includes a Sequence Listing.

(56) References Cited

OTHER PUBLICATIONS

Dornadula, G., et al., Residual HIV-1 RNA in blood plasma of patients taking suppressive highly active antiretroviral therapy. JAMA, 1999. 282(17): p. 1627-32.
Douek, D.C., et al., HIV preferentially infects HIV-specific CD4+ T cells. Nature, 2002. 417(6884): p. 95-8.
Drosten et al., Topographic and Quantitative Display of Integrated Human Immunodeficiency Virus-1 Provirus DNA in Human Lymph Nodes by Real-Time Polymerase Chain Reaction, J Mol Diagn. May 2005; 7(2): 219-225.
Drosten et al., Ultrasensitive Monitoring of HIV-1 Viral Load by a Low-Cost Real-Time Reverse Transcription-PCR Assay with Internal Control for the 5' Long Terminal Repeat Domain, 2006 Clinical Chemistry 52:7: 1258-66 (2006).
Duncan et al., High-Multiplicity HIV-1 Infection and Neutralizing Antibody Evasion Mediated by the Macrophage-T Cell Virological Synapse, J Virol. Feb. 2014; 88(4): 2025-2034.
EASL International Consensus Conference on Hepatitis C. Paris, Feb. 26-27, 1999. Consensus statement. J Hepatol, 1999. 31 Suppl 1: p. 3-8.
Espy, M.J., et al., Real-time PCR in clinical microbiology: applications for routine laboratory testing. Clin Microbiol Rev, 2006. 19(1): p. 165-256.
Fiebig, E.W., et al., Dynamics of HIV viremia and antibody seroconversion in plasma donors: implications for diagnosis and staging of primary HIV infection. AIDS, 2003. 17(13): p. 1871-9.
Finley et al., Transcriptional regulation of the major HIV-1 coreceptor, CXCR4, by the k opioid receptor, 2011 J Leukoc bio. 90(1):111-121.
Finzi, D., et al., Identification of a reservoir for HIV-1 in patients on highly active antiretroviral therapy. Science, 1997. 278: p. 1295-1300.
Finzi, D., et al., Latent infection of CD4+ T cells provides a mechanism for lifelong persistence of HIV-1, even in patients on effective combination therapy. Nat. Med., 1999. 5(5): p. 512-7.
Fried, M.W., et al., Peginterferon alfa-2a plus ribavirin for chronic hepatitis C virus infection. N Engl J Med, 2002. 347 (13): p. 975-82.
Fukai et al., Association Between Lamivudine Sensitivity and the Number of Substitutions in the Reverse Transcriptase Region of the Hepatitis B Virus Polymerase, J Viral Hepat. 2007;14(9):661-666.
Graf, E.H., et al., Elite suppressors harbor low levels of integrated HIV DNA and high levels of 2-LTR circular HIV DNA compared to HIV+ patients on and off HAART. PLoS Pathog, 2011. 7(2): p. e1001300.
Gulick, R.M., et al., Treatment with indinavir, zidovudine, and lamivudine in adults with human immunodeficiency virus infection and prior antiretroviral therapy. N. Engl. J. Med., 1997. 337(11): p. 734-739.
Habbal, Wafa., English Abstract of PhD Thesis of Wafa Habbal: Comparative Analysis of Some Pathogenic Virus Genomes; Diagnosis and Typing by Laboratory Techniques &Viral Bioinformatics (2012). See pp. 139-140.
Hammer, S.M., et al., A controlled trial of two nucleoside analogues plus indinavir in persons with human immunodeficiency virus infection and CD4 cell counts of 200 per cubic millimeter or less. N Engl J Med, 1997. 337(11): p. 725-733.
Henderson, Identification of Novel T Cell Factor 4 (TCF-4) Binding Sites on the HIV Long Terminal Repeat Which Associate with TCF-4, B-Catenin, and SMAR1 to Repress HIV Transcription, 2012 J. Virol. vol. 86 No. 17: 9495-9503.
Hutter, G., et al., Long-term control of HIV by CCR5 Delta32/Delta32 stem-cell transplantation. N Engl J Med, 2009. 360(7): p. 692-8.
Iloeje, U.H., et al., Risk and predictors of mortality associated with chronic hepatitis B infection. Clin Gastroenterol Hepatol, 2007. 5(8): p. 921-31.
Jaeckel, E., et al., Treatment of acute hepatitis C with interferon alfa-2b. N Engl J Med, 2001. 345(20): p. 1452-7.
Kobayashi, S., et al., Development of hepatocellular carcinoma in patients with chronic hepatitis C who had a sustained virological response to interferon therapy: a multicenter, retrospective cohort study of 1124 patients. Liver Int, 2007. 27(2): p. 186-91.
Lok, A.S. and B.J. McMahon, Chronic hepatitis B. Hepatology, 2007.45(2): p. 507-39.
Makiyama, A., et al., Characteristics of patients with chronic hepatitis C who develop hepatocellular carcinoma after a sustained response to interferon therapy. Cancer, 2004. 101(7): p. 1616-22.
Morgan, T.R., et al., Outcome of sustained virological responders with histologically advanced chronic hepatitis C. Hepatology, 2010. 52(3): p. 833-44.
O'Doherty, U., et al., A sensitive, quantitative assay for human immunodeficiency virus type 1 integration. J Virol, 2002. 76(21): p. 10942-50.
Perelson, A.S., et al., Decay characteristics of HIV-1-infected compartments during combination therapy. Nature, 1997. 387: p. 188-191.
Richman, D.D., et al., The challenge of finding a cure for HIV infection. Science, 2009. 323(5919): p. 1304-7.
Rousseau et al., Large-scale amplification, cloning and sequencing of near full-length HIV-1 subtype C genomes, Journal of Virological Methods 136 (2006) 118-125.
Saez-Cirion, A., et al., Post-treatment HIV-1 controllers with a long-term virological remission after the interruption of early initiated antiretroviral therapy ANRS VISCONTI Study. PLoS Pathog, 2013. 9(3): p. e1003211.
Scherzer, T.M., et al., Hepatocellular carcinoma in long-term sustained virological responders following antiviral combination therapy for chronic hepatitis C. J Viral Hepat, 2008. 15(9): p. 659-65.
Scriba et al., Characterization of the South African HIV Type 1 Subtype C Complete 59 Long Terminal Repeat, nef, and Regulatory Genes, AIDS Research and Human Retroviruses vol. 18, No. 2, 2002, pp. 149-159.
Sewell, J.L., K.M. Stick, and A. Monto, Hepatocellular carcinoma after sustained virologic response in hepatitis C patients without cirrhosis on a pretreatment liver biopsy. Eur J Gastroenterol Hepatol, 2009. 21(2): p. 225-9.
Siliciano, J.D., et al., Long-term follow-up studies confirm the stability of the latent reservoir for HIV-1 in resting CD4+ T cells. Nat Med, 2003. 9(6): p. 727-8.
Steele et al., u-opioid modulation of HIV-1 coreceptor expression and HIV-1 replication, 2003 Virology vol. 309 Issue 1: 99-107.
Sulkowski, M.S., et al., Daclatasvir plus sofosbuvir for previously treated or untreated chronic HCV infection. N Engl J Med, 2014. 370(3): p. 211-21.
Szabo et al., Selective inactivation of CCR5 and decreased infectivity of R5 HIV-1 strains mediated by opioid-induced heterologous desensitization, 2003 Journal of Leukocyte Biology vol. 74: 1076-82.
Tzitzivacos, Dissertation of Dr D.B.Tzitzivacos: Viral Genetic Determinants of Nonprogressive HIV-1 Subtype C Infection in Antiretroviral Drug Naïve Children, Nov. 2008, Department of Molecular Medicine and Haematology, Faculty of Health Sciences, University of the Witwatersrand Medical School, Johannesburg.
Van Der Meer, A.J., et al., Association between sustained virological response and allcause mortality among patients with chronic hepatitis C and advanced hepatic fibrosis. JAMA, 2012. 308(24): p. 2584-93.
Wang et al., MicroRNA-581 Promotes Hepatitis B Virus Surface Antigen Expression by Targeting Dicer and EDEM1, Carcinogenesis, CARCIN-2013-01178.R2, May 14, 2014.
Wong, J.K., et al., Recovery of replication-competent HIV despite prolonged suppression of plasma viremia. Science, 1997. 278: p. 1291-1300.
Yu, J.J., et al., A more precise HIV integration assay designed to detect small differences finds lower levels of integrated DNA in HART treated patients. Virology, 2008. 379(1): p. 78-86.
Zhang et al., Analysis of the complete hepatitis B virus genome in patients with genotype C chronic hepatitis and hepatocellular carcinoma. Cancer Science, vol. 98, Issue 12, pp. 1921-1929, Dec. 2007.
Zhu, T., et al., Evidence for Human Immunodeficiency Virus Type 1 Replication In Vivo in CD14+ Monocytes and Its Potential Role

(56) References Cited

OTHER PUBLICATIONS as a Source of Virus in Patients on Highly Active Antiretroviral Therapy. J. Virol., 2002. 76(2): p. 707-716.

Zhu, T., et al., Persistence of Extraordinarily Low Levels of Genetic Homogeneous Human Immunodeficiency Virus type 1 in Exposed Seronegative Individuals. J. Virol., 2003. 77(11): p. 6108-6116.

* cited by examiner

SEQUENCE LISTING

```
<160> NUMBER OF SEQ ID NOS: 35

<210> SEQ ID NO 1
<211> LENGTH: 26
<212> TYPE: DNA
<213> ORGANISM: artificial sequence
<220> FEATURE:
<223> OTHER INFORMATION: primer

<400> SEQUENCE: 1
tctggctaac tagggaaccc actgct                                          26

<210> SEQ ID NO 2
<211> LENGTH: 26
<212> TYPE: DNA
<213> ORGANISM: artificial sequence
<220> FEATURE:
<223> OTHER INFORMATION: primer

<400> SEQUENCE: 2
tgcgcgcttc aagccgagtc ctgcgt                                          26

<210> SEQ ID NO 3
<211> LENGTH: 32
<212> TYPE: DNA
<213> ORGANISM: artificial sequence
<220> FEATURE:
<223> OTHER INFORMATION: primer

<400> SEQUENCE: 3
agggaaccca ctgcttaagc ctcaataaag ct                                   32
```

```
<210> SEQ ID NO 4
<211> LENGTH: 24
<212> TYPE: DNA
<213> ORGANISM: artificial sequence
<220> FEATURE:
<223> OTHER INFORMATION: primer

<400> SEQUENCE: 4
agcaagccga gtcctgcgtc gaga                                              24

<210> SEQ ID NO 5
<211> LENGTH: 20
<212> TYPE: DNA
<213> ORGANISM: artificial sequence
<220> FEATURE:
<223> OTHER INFORMATION: primer

<400> SEQUENCE: 5
agcctcaata aagcttgcct                                                   20

<210> SEQ ID NO 6
<211> LENGTH: 23
<212> TYPE: DNA
<213> ORGANISM: artificial sequence
<220> FEATURE:
<223> OTHER INFORMATION: primer

<400> SEQUENCE: 6
ccgccactgc tagagatttt cca                                               23

<210> SEQ ID NO 7
<211> LENGTH: 20
<212> TYPE: DNA
<213> ORGANISM: artificial sequence
<220> FEATURE:
<223> OTHER INFORMATION: probe

<400> SEQUENCE: 7
tctggtaact agagatccct                                                   20

<210> SEQ ID NO 8
<211> LENGTH: 28
<212> TYPE: DNA
<213> ORGANISM: artificial sequence
<220> FEATURE:
<223> OTHER INFORMATION: primer

<400> SEQUENCE: 8
ggttagacca gatctgagcc tgggagct                                          28

<210> SEQ ID NO 9
<211> LENGTH: 33
<212> TYPE: DNA
<213> ORGANISM: artificial sequence
<220> FEATURE:
<223> OTHER INFORMATION: primer

<400> SEQUENCE: 9
ggaacccact gcttaagcct caataaagct tgc                                    33

<210> SEQ ID NO 10
<211> LENGTH: 23
<212> TYPE: DNA
<213> ORGANISM: artificial sequence
<220> FEATURE:
<223> OTHER INFORMATION: primer
```

```
<400> SEQUENCE: 10
tgttcgggcg ccactgctag aga                                    23

<210> SEQ ID NO 11
<211> LENGTH: 24
<212> TYPE: DNA
<213> ORGANISM: artificial sequence
<220> FEATURE:
<223> OTHER INFORMATION: primer

<400> SEQUENCE: 11
aagcctcaat aaagcttgcc ttga                                   24

<210> SEQ ID NO 12
<211> LENGTH: 29
<212> TYPE: DNA
<213> ORGANISM: artificial sequence
<220> FEATURE:
<223> OTHER INFORMATION: primer

<400> SEQUENCE: 12
agggtctgag ggatctctag ttaccagag                              29

<210> SEQ ID NO 13
<211> LENGTH: 18
<212> TYPE: DNA
<213> ORGANISM: artificial sequence
<220> FEATURE:
<223> OTHER INFORMATION: probe

<400> SEQUENCE: 13
ttcaagtagt gtgtgccc                                          18

<210> SEQ ID NO 14
<211> LENGTH: 18
<212> TYPE: DNA
<213> ORGANISM: artificial sequence
<220> FEATURE:
<223> OTHER INFORMATION: probe

<400> SEQUENCE: 14
agtagtgtgt gcccgtct                                          18

<210> SEQ ID NO 15
<211> LENGTH: 18
<212> TYPE: DNA
<213> ORGANISM: artificial sequence
<220> FEATURE:
<223> OTHER INFORMATION: probe

<400> SEQUENCE: 15
tagtgtgtgc ccgtctgt                                          18

<210> SEQ ID NO 16
<211> LENGTH: 22
<212> TYPE: DNA
<213> ORGANISM: artificial sequence
<220> FEATURE:
<223> OTHER INFORMATION: primer

<400> SEQUENCE: 16
cccctcccgg gagagccata gt                                     22

<210> SEQ ID NO 17
```

<210> SEQ ID NO 17
<211> LENGTH: 31
<212> TYPE: DNA
<213> ORGANISM: artificial sequence
<220> FEATURE:
<223> OTHER INFORMATION: primer

<400> SEQUENCE: 17
gcaccctatc aggcagtacc acaaggcctt t                          31

<210> SEQ ID NO 18
<211> LENGTH: 26
<212> TYPE: DNA
<213> ORGANISM: artificial sequence
<220> FEATURE:
<223> OTHER INFORMATION: primer

<400> SEQUENCE: 18
cccccctccc gggagagcca tagtgg                                26

<210> SEQ ID NO 19
<211> LENGTH: 21
<212> TYPE: DNA
<213> ORGANISM: artificial sequence
<220> FEATURE:
<223> OTHER INFORMATION: primer

<400> SEQUENCE: 19
ctcgcggggg cacgcccaaa t                                     21

<210> SEQ ID NO 20
<211> LENGTH: 18
<212> TYPE: DNA
<213> ORGANISM: artificial sequence
<220> FEATURE:
<223> OTHER INFORMATION: primer

<400> SEQUENCE: 20
tcccgggaga gccatagt                                         18

<210> SEQ ID NO 21
<211> LENGTH: 22
<212> TYPE: DNA
<213> ORGANISM: artificial sequence
<220> FEATURE:
<223> OTHER INFORMATION: primer

<400> SEQUENCE: 21
gggtttatcc aagaaaggac cc                                    22

<210> SEQ ID NO 22
<211> LENGTH: 19
<212> TYPE: DNA
<213> ORGANISM: artificial sequenceq
<220> FEATURE:
<223> OTHER INFORMATION: probe

<400> SEQUENCE: 22
tgcggaaccg gtgagtmgb                                        19

<210> SEQ ID NO 23
<211> LENGTH: 19
<212> TYPE: DNA
<213> ORGANISM: artificial sequence
<220> FEATURE:
<223> OTHER INFORMATION: primer

<400> SEQUENCE: 23

```
tgcggaaccg gtgagtmgb                                                    19

<210> SEQ ID NO 24
<211> LENGTH: 18
<212> TYPE: DNA
<213> ORGANISM: artificial sequence
<220> FEATURE:
<223> OTHER INFORMATION: primer

<400> SEQUENCE: 24
gcgggggcac gcccaaat                                                     18

<210> SEQ ID NO 25
<211> LENGTH: 16
<212> TYPE: DNA
<213> ORGANISM: artificial sequence
<220> FEATURE:
<223> OTHER INFORMATION: primer

<400> SEQUENCE: 25
tctgcggaac cggtga                                                       16

<210> SEQ ID NO 26
<211> LENGTH: 16
<212> TYPE: DNA
<213> ORGANISM: artificial sequence
<220> FEATURE:
<223> OTHER INFORMATION: primer

<400> SEQUENCE: 26
ctgcggaacc ggtgag                                                       16

<210> SEQ ID NO 27
<211> LENGTH: 22
<212> TYPE: DNA
<213> ORGANISM: artificial sequence
<220> FEATURE:
<223> OTHER INFORMATION: primer

<400> SEQUENCE: 27
cctatcaggc agtaccacaa gg                                                22

<210> SEQ ID NO 28
<211> LENGTH: 20
<212> TYPE: DNA
<213> ORGANISM: artificial sequence
<220> FEATURE:
<223> OTHER INFORMATION: primer

<400> SEQUENCE: 28
agtaccacaa ggcctttcgc                                                   20

<210> SEQ ID NO 29
<211> LENGTH: 21
<212> TYPE: DNA
<213> ORGANISM: artificial sequence
<220> FEATURE:
<223> OTHER INFORMATION: primer

<400> SEQUENCE: 29
caccctatca ggcagtacca c                                                 21

<210> SEQ ID NO 30
<211> LENGTH: 19
<212> TYPE: DNA
```

```
<213> ORGANISM: artificial sequence
<220> FEATURE:
<223> OTHER INFORMATION: primer

<400> SEQUENCE: 30
tcaggcagta ccacaaggc                                              19

<210> SEQ ID NO 31
<211> LENGTH: 26
<212> TYPE: DNA
<213> ORGANISM: artificial sequence
<220> FEATURE:
<223> OTHER INFORMATION: primer

<400> SEQUENCE: 31
cactcccctg tgaggaacta ctgtct                                      26

<210> SEQ ID NO 32
<211> LENGTH: 25
<212> TYPE: DNA
<213> ORGANISM: artificial sequence
<220> FEATURE:
<223> OTHER INFORMATION: primer

<400> SEQUENCE: 32
tggtgcacgg tctacgagac ctccc                                       25

<210> SEQ ID NO 33
<211> LENGTH: 18
<212> TYPE: DNA
<213> ORGANISM: artificial sequence
<220> FEATURE:
<223> OTHER INFORMATION: primer

<400> SEQUENCE: 33
gcctgggttc cctgttcc                                               18

<210> SEQ ID NO 34
<211> LENGTH: 19
<212> TYPE: DNA
<213> ORGANISM: artificial sequence
<220> FEATURE:
<223> OTHER INFORMATION: primer

<400> SEQUENCE: 34
cgacgtaccc ctgacatgg                                              19

<210> SEQ ID NO 35
<211> LENGTH: 26
<212> TYPE: DNA
<213> ORGANISM: artificial sequence
<220> FEATURE:
<223> OTHER INFORMATION: probe

<400> SEQUENCE: 35
ccaggccaat gtctcaccaa gctctg                                      26
```

PRIMERS, PROBES AND METHODS FOR SENSITIVE, SPECIFIC DETECTION AND MONITORING OF HIV-1 AND HCV

This application claims benefit of U.S. provisional patent application No. 62/119,672, filed Feb. 23, 2015, the entire contents of which are incorporated by reference into this application.

ACKNOWLEDGEMENT OF GOVERNMENT SUPPORT

This invention was made with government support under Grant Nos. AI045402 and AI055336, awarded by the National Institutes of Health. The US Government has certain rights in the invention.

REFERENCE TO A SEQUENCE LISTING SUBMITTED VIA EFS-WEB

The content of the ASCII text file of the sequence listing named "UW56WOU1_SL", which is 7 kb in size, was created on Feb. 22, 2016, and electronically submitted via EFS-Web herewith the application. The sequence listing is incorporated herein by reference in its entirety.

TECHNICAL FIELD OF THE INVENTION

The present invention relates to nucleic acid primers, probes, and amplification methods for detection and monitoring of HIV-1 RNA and DNA, and HCV RNA in samples, as well as compositions for performing these methods including primers, probes. RNA and DNA extraction, PCR mixtures, assay standards, controls and amplification cycles.

BACKGROUND OF THE INVENTION

Real-time PCR is currently the preferred method for quantitation of HIV-1 RNA/DNA and HCV RNA [1-9]. However, despite their accuracy and specificity, real-time PCR methods using the real-time PCR detection are unable to reliably quantify 100 copies or less of HIV-1 RNA/DNA target per reaction in the context of total RNA/DNA in cells and clinical samples [10]. This evokes the possibility of yielding false-negative results and failure in precisely quantifying low levels of target genes when clinical samples from patients are studied, especially when limited amounts of clinical material are available for analysis. Beyond real-time PCR techniques is Nested PCR [11]. While it is considered a more sensitive method than real-time PCR it requires labor-intensive and time-consuming experimental procedures. More importantly, the nested PCR protocols can introduce contamination by opening the first round PCR tube and transferring first round PCR products to the second round PCR [11], which does not meet the need of "closed" PCR system for clinical use.

Highly active antiretroviral therapy (HAART) can reduce patient's blood plasma HIV-1 RNA to levels below the detection limit of clinical assays (20-50 copies of HIV-1 RNA/ml) including the Roche Taqman PCR and Abbott HIV-1 Reagent Kit that are widely used and considered the gold standard of HIV assays [12-17]. The effective suppression of viremia initially encouraged hope that the virus could be eradicated with 2-3 years of HAART [14]. Treatment outcomes are classified into "sterilization cure" or "functional cure". A sterilization cure occurs when not only HIV-1 DNA and RNA becomes undetectable in samples from the treated patient but also when the patient remains free from disease over a prolonged period without antiretroviral treatment. The first reported case of a sterilization cure of HIV was an adult who underwent stem cell transplants [18]. A functional cure occurs when low grade HIV-1 DNA and/or RNA is detectable in the treated patient but the patient remains free of HIV-associated disease over a prolonged period of time. Elite controllers of HIV-1 infection are considered prototype cases of a functional cure against HIV [4, 19, 20].

However, a latent form of HIV-1 persists in vivo in patients treated with HAART [12-17]. A small fraction of resting memory CD4+ T cells carry integrated viral genomes. These cells do not produce virus particles while in the resting state, but can give rise to replication-competent virus following cellular activation [11, 15]. These latently infected cells are rare but stable, even in patients on prolonged HAART [17, 21-23]. Interruption of HAART leads to a virus rebound in most patients [24, 25]. This latent reservoir is widely recognized as the major barrier to HIV-1 eradication or cure [26].

A major question for clinical trials of antiretroviral therapy or eradication strategies is how to evaluate the effectiveness of anti-HIV therapy. The residual viremia (HIV-1 RNA) is an important indication of ongoing virus production. Several studies have shown that residual viremia is not reduced by treatment intensification [27], and thus it is likely to reflect virus production from stable reservoirs. For example, residual viremia could in part reflect virus production by latently infected cells that have become activated. HIV-1 RNA and DNA remain the most sensitive measure of residual infection, but the low levels of residual virus in the context of large amount of cells and related materials present challenges to detect and to quantify precisely. There is also no HIV-1 DNA quantitative assay approved for use as a clinical test. The development of a high-throughput scalable and sensitive assay to measure the residual HIV-1 RNA and DNA in patients has been identified as a key priority in HIV-1 antiretroviral therapy and eradication research [28].

Similarly, HCV RNA viral loads are assessed in patients with HCV infection when monitoring for responses to antiviral therapy. Patients who remain negative for HCV RNA six months after completing therapy for HCV infection remain free of the virus in the longer term and have achieved a sustained virologic response (SVR) [29]. However, clinically diagnosed SVR or even "cure" achievement does not universally prevent progression to liver diseases, such as liver cancer [30-35]. Contrary to prevailing opinion based on the currently available clinical testing for HCV RNA, clinical diagnosis of SVR does not reflect molecular eradication of HCV [8-14]. Thus, even in the wake of new "cure" drugs such as Gilead's sofosbuvir, which was recently approved by the FDA, continuous monitoring of extremely low levels of HCV RNA by more sensitive PCR for a longer time (or lifelong) is still needed [36].

HIV-1 infection is currently diagnosed by positive HIV antibodies detected by ELISA and Western Blot. However, after HIV acquisition, HIV antibodies are typically not detected for a month, or as long as 6 months or for an even longer time in patients with Immunodeficiency [37]. During this "window period" of acute HIV-1 infection (AHI) (from HIV infection to initial HIV antibody detection), HIV-1 RNA and DNA in blood can be detected by PCR initially at low levels during the first few days and weeks, increases rapidly and then reaches peak levels at time when HIV antibodies are first detected. Despite infection of nearly 60 million individuals worldwide with HIV, fewer than 1,000 cases have been diagnosed in the first month of infection.

Detection of AHI is important for several reasons. First, very early recognition may allow for HIV treatment that could alter the natural history of disease, or even potentially cure HIV-1 infection [38]. Second, prevention strategies directed at subjects with AHI may have great impact. AHI with high viral load at weeks 3-4 before diagnosis by antibody test have a significantly higher chance of transmitting HIV to their sexual partners.

Detection of AHI is doable, but needs significant improvement. There is a lack of a sensitive test to identify HIV infection at an early stage. PCR assays have not traditionally been used for routine clinical HIV screening, but is currently recommended, particularly for the blood bank in USA and other countries.

Similarly, acute early HCV infection is also rarely detected. The acute form of the disease leads to chronic hepatitis in the majority of cases. Due to the higher chance of transmitting HCV to others and progressive diseases in the chronic phase, recognizing acute hepatitis is critical. Sensitive HCV RNA assay is needed as HCV presents in most case in humans at low levels or remains a silent infection.

Tests for antibodies to HIV do not establish the presence of HIV infection in infants because of transplacental transfer of maternal antibodies to HIV; therefore, a virologic test, particularly with higher sensitivity and specificity, should be used [39, 40]. Positive virologic tests include HIV DNA assays, and related RNA assays.

Antibody-based HCV tests should not be used in infants younger than 18 months given the likelihood of reactivity due to maternal antibody. In this case, HCV RNA should be used for diagnosis of HCV infection. In addition, there are children infected with HCV by mother-to-child transmission who remained persistently seronegative despite the presence of high levels of circulating HCV RNA. HCV RNA is therefore important in diagnosis of HCV infection in children. A sensitive and qualitative test for HCV-RNA is currently required to confirm active HCV infection as only small samples from infants are typically available [41, 42].

SUMMARY OF THE INVENTION

The ultrasensitive PCR (Ultra PCR) methods described herein provide more sensitive and specific HIV and HCV detection than currently available assays. The methods are also capable of precise quantification, and of detecting different subtypes of HIV and HCV.

In one embodiment, the invention provides an oligonucleotide composition comprising a nucleic acid sequence selected from the group consisting of SEQ ID NOS:1-30, complementary sequences thereof, active fragments, and combinations thereof. In one embodiment the invention provides a collection of oligonucleotides for amplifying a portion of HIV-1 genomic sequence. The collection comprises one or more forward primers selected from the group consisting of SEQ ID NO:1, SEQ ID NO:3, SEQ ID NO:5, SEQ ID NO:8, SEQ ID NO:9, SEQ ID NO: 11, complementary sequences thereof, active fragments thereof, and combinations thereof; one or more reverse primers selected from the group consisting of SEQ ID NO:2, SEQ ID NO:4, SEQ ID NO:6, SEQ ID NO:10, SEQ ID NO:12, complementary sequences thereof, active fragments thereof, and combinations thereof; and one or more probes selected from the group consisting of SEQ ID NO:7, SEQ ID NO:13, SEQ ID NO:14, SEQ ID NO:15, complementary sequences thereof, active fragments thereof, and combinations thereof. In one embodiment, the one or more forward primers comprise SEQ ID NO:1, SEQ ID NO:3, and SEQ ID NO:5 or active fragments thereof; the one or more reverse primers comprise SEQ ID NO:2, SEQ ID NO:4, and SEQ ID NO:6 or active fragments thereof; and the one or more probes comprise SEQ ID NO:7, or active fragments thereof. The collection of oligonucleotides can comprise an outer, middle and inner set of primers, wherein the outer primers comprise SEQ ID NO:1, SEQ ID NO:2 or active fragments thereof; the middle primers comprise SEQ ID NO:3, SEQ ID NO:4, or active fragments thereof; and the inner primers comprise SEQ ID NO: 5, SEQ ID NO: 6 or active fragments thereof; and the one or more probes comprise SEQ ID NO:7, or active fragments thereof. In another embodiment, the one or more forward primers comprise SEQ ID NO:8, SEQ ID NO:9, SEQ ID NO:11, or active fragments thereof; the one or more reverse primers comprise SEQ ID NO:2, SEQ ID NO:10, SEQ ID NO:12 or active fragments thereof; the one or more probes are selected from the group consisting of SEQ ID NO:13, SEQ ID NO:14, SEQ ID NO:15, and active fragments thereof. The collection of oligonucleotides can comprise an outer, middle and inner set of primers, wherein the outer primers comprise SEQ ID NO:8, SEQ ID NO:2 or active fragments thereof; the middle primers comprise SEQ ID NO:9, SEQ ID NO:10 or active fragments thereof; the inner primers comprise SEQ ID NO:11, SEQ ID NO:12 or active fragments thereof; and the one or more probes are selected from the group consisting of SEQ ID NO:13, SEQ ID NO:14, SEQ ID NO:15, and active fragments thereof.

The invention additionally provides a collection of oligonucleotides for amplifying a portion of HCV genomic sequence. In one embodiment, the collection comprises one or more forward primers selected from the group consisting of SEQ ID NO:16, SEQ ID NO:18. SEQ ID NO:20, complementary sequences thereof, active fragments thereof, and combinations thereof; one or more reverse primers selected from the group consisting of SEQ ID NO:17, SEQ ID NO:19, SEQ ID NO:21, SEQ ID NO:23, SEQ ID NO:24, SEQ ID NO: 27, SEQ ID NO: 28, SEQ ID NO: 29, SEQ ID NO: 30, complementary sequences thereof, active fragments thereof, and combinations thereof: and one or more probes selected from the group consisting of SEQ ID NO:22, SEQ ID NO:25, SEQ ID NO:26, complementary sequences thereof, active fragments thereof, and combinations thereof. In one embodiment, the one or more forward primers comprise SEQ ID NO:16, SEQ ID NO:18, SEQ ID NO:20, or active fragments thereof, and the one or more reverse primers comprise SEQ ID NO:17, SEQ ID NO:19, SEQ ID NO:21, or active fragments thereof, and the probe comprises SEQ ID NO:22, or active fragments thereof. The collection of oligonucleotides can comprise an outer, middle and inner set of primers, wherein the outer primers comprise SEQ ID NO:16, SEQ ID NO:17 or active fragments thereof; the middle primers comprise SEQ ID NO:18, SEQ ID NO: 19 or active fragments thereof; the inner primers comprise SEQ ID NO:20, SEQ ID NO:21 or active fragments thereof; and the one or more probes selected from the group consisting of SEQ ID NO:22, or active fragments thereof. In one embodiment, the one or more forward primers comprise SEQ ID NO:16, SEQ ID NO: 18, SEQ ID NO:20, or active fragments thereof: and the one or more reverse primers comprise SEQ ID NO:23, SEQ ID NO:24, SEQ ID NO:21, or active fragments thereof; and the one or more probes comprise SEQ ID NO:25, SEQ ID NO:26, or active fragments thereof. The collection of oligonucleotides can comprise an outer, middle and inner set of primers, wherein the outer primers comprise SEQ ID NO:16, SEQ ID NO:23 or active fragments thereof: the middle primers comprise SEQ ID NO:18, SEQ ID NO:24 or active fragments thereof: the inner primers comprise SEQ ID NO:20, SEQ ID NO:21 or active fragments thereof; and one or more probes comprise SEQ ID NO:25, SEQ ID NO:26, or active fragments thereof.

The invention also provides a kit for amplifying HIV by PCR comprising a set of oligonucleotides. In one embodiment, the set of PCR oligonucleotides comprises a collection of oligonucleotides as defined above. In one embodiment, the PCR is triple nested PCR.

The invention further provides a kit for amplifying HCV by PCR. The kit comprises a set of PCR oligonucleotides, wherein the PCR oligonucleotides comprises a collection of oligonucleotides as defined above. In one embodiment, the PCR is triple nested PCR.

Also provided is a method for detecting an RNA virus in a sample. In one embodiment, the method comprises isolating RNA in a sample, submitting the isolated RNA to reverse transcription PCR, contacting the resulting reverse transcription PCR product with a set of primers as described herein, and submitting the resulting mixture to one or more nucleic acid amplification reactions. The invention also provides a method for detecting HIV-1 in a sample. In one embodiment, the method comprises isolating RNA in a sample, submitting the isolated RNA to reverse transcription PCR, contacting the resulting reverse transcription PCR product with a set of primers as described in Table 1, and submitting the resulting mixture to one or more nucleic acid amplification reactions. In one embodiment, the invention provides a method for detecting HIV-1 in a sample, wherein the method comprises isolating RNA in a sample, submitting the isolated RNA to reverse transcription PCR, contacting the resulting reverse transcription PCR product with a set of outer primers, and submitting the resulting mixture to a first nucleic acid amplification reaction, wherein the set of primers comprises a combination of oligonucleotides as defined in Table 1. Optionally, the method further comprises contacting a product from the first nucleic acid amplification reaction with a set of middle primers and submitting the resulting mixture to a second nucleic acid amplification reaction. The method can further comprise contacting a product from the second nucleic acid amplification reaction with a set of inner primers and submitting the resulting mixture to a third nucleic acid amplification reaction. The method optionally further comprises contacting a product from the third nucleic amplification reaction with the probe for quantitation by real time PCR.

The invention additionally provides a method for detecting HCV in a sample comprising: isolating RNA in a sample, submitting the isolated RNA to reverse transcription PCR, contacting the resulting reverse transcription PCR product with a set of primers as described in Table 2, and submitting the resulting mixture to one or more nucleic acid amplification reactions. In one embodiment, the invention provides a method for detecting HCV in a sample comprising: isolating RNA in a sample, submitting the isolated RNA to reverse transcription PCR, contacting the resulting reverse transcription PCR product with a set of outer primers, and submitting the resulting mixture to a first nucleic acid amplification reaction, wherein the set of primers comprises a combination of oligonucleotides as defined in Table 2. The method optionally further comprises contacting a product from the first nucleic acid amplification reaction with a set of middle primers and submitting the resulting mixture to a second nucleic acid amplification reaction. Optionally, the method further comprises contacting a product from the second nucleic acid amplification reaction with a set of inner primers and submitting the resulting mixture to a third nucleic acid amplification reaction. The method can further comprise contacting a product from the third nucleic amplification reaction with the probe for quantitation by real time PCR.

The invention further provides a method for detecting HCV in a sample comprising: isolating RNA in a sample, submitting the isolated RNA to reverse transcription PCR, contacting the resulting reverse transcription PCR product with a set of outer primers, and submitting the resulting mixture to a first nucleic acid amplification reaction, wherein the primers comprises a combination of oligonucleotides as defined in Table 2. In one embodiment, the method further comprises contacting a product from the first nucleic acid amplification reaction with a set of middle primers and submitting the resulting mixture to a second nucleic acid amplification reaction. The method can further comprise contacting a product from the second nucleic acid amplification reaction with a set of inner primers and submitting the resulting mixture to a third nucleic acid amplification reaction. In one embodiment, the method further comprises contacting a product from the third nucleic amplification reaction with the probe for quantitation by real time PCR.

In the methods described herein, the first nucleic acid amplification reaction is typically performed at a temperature of about 65-72° C., the second nucleic acid amplification reaction is typically performed at a temperature of about 60-64° C. such as about 62° C., and the third nucleic acid amplification reaction is typically performed at a temperature of about 50-55° C., such as about 52° C. Optionally, the method is carried out in a single tube.

In some embodiments, the RNA virus is HIV and/or HCV. In some embodiments, the sample contains less than 5 copies of the RNA virus. In one embodiment, the HIV is HIV-1. Examples of the HIV-1 include, but are not limited to, HIV-1 subtypes of the M or O groups.

The invention further provides a method for monitoring the efficacy of anti-retroviral treatment in a subject infected with HIV or HCV. In one embodiment, the method comprises subjecting a sample obtained from the subject to a method for detecting an RNA virus as described herein; and determining whether the sample contains fewer copies of the virus per milliliter than a predetermined threshold. A reduction in copies of the virus per milliliter sample is indicative of effective anti-retroviral treatment. In one embodiment, the predetermined threshold is an amount detected in a prior sample obtained from the subject at a previous time point. In one embodiment, the predetermined threshold is 5 copies of virus per milliliter sample.

The invention additionally provides a method for detecting acute HIV-1 infection in a subject. In one embodiment, the method comprises subjecting a sample obtained from the subject to a method of detecting HIV described herein; and determining whether the sample contains a detectable amount of HIV-1 DNA or RNA. The presence of a detectable amount of HIV-1 DNA or RNA is indicative of acute HIV-1 infection.

The invention also provides a method for detecting acute early HCV infection in a subject. In one embodiment, the method comprises subjecting a sample obtained from the subject to a method of detecting HCV as described herein: and determining whether the sample contains a detectable amount of HCV RNA. The presence of a detectable amount of HCV RNA is indicative of acute early HCV infection.

For use in the methods described herein, representative examples of the sample include, but are not limited to, blood, plasma or serum, saliva, urine, cerebral spinal fluid, milk, cervical secretions, semen, tissue, cell cultures, and the like.

DESCRIPTION OF THE DRAWINGS

FIG. 1A is a Standard Curve of the HIV-1 RNA Assay Standards 4, 40, 400, 4E3, 4E4, 4E5 copies used in the HIV-1 Ultra PCR for determining quantities of samples. Copies/mL (X axis) plotted against Cycle Number (Ct) determines slope of line used to determine sample quantity. R2 value of 0.997 indicates a high degree of linearity of the standards over this range. An R2 of 1.0 is perfect: anything over 0.95 is considered acceptable. FIG. 1B is an Amplification plot of the HIV-1 RNA Assay standards used to determine the standard curve and evaluate the exponential growth of signal during PCR. Each standard was tested in duplicate, and the thick horizontal line is the threshold set to determine the Ct value for all standards used to determine the line in FIG. 1A. FIG. 1C is an Amplification plot of the VQA positive controls run in same plate with samples, which validate the PCR reactions in each run. The nominal quantity of VQA positive controls are 0 (negative), 200 copies (2E2), 1500 copies (1.5E3), and 15,000 copies (1.5E4) per ml. Each dilution was tested by Ultra PCR in duplicate. Threshold set to 0.2 for each run. The cycle numbers, a cross point with the threshold 0.2 (thick horizontal line) for each VQA was used to determine its quantity. FIG. 1D is an Amplification plot of the WHO International Standard of HIV-1 RNA with nominal quantities of 2.2E3, 2.2E2, 2.2 E1, and 2.2 copies/ml. Each dilution is tested in duplicate. The cycle numbers, a cross point with the threshold 0.2 (thick horizontal line) for each sample was used to determine its quantity. Excellent correlations were observed between the nominal quantities of the WHO International Standards and VQA with the copy numbers produced by Ultra PCR with primers/probe set #1, which indicate accurate quantification of HIV-1 Ultra PCR.

FIG. 2A is a Standard curve of pAW RNA using 5E2, 5E3, and 5E4 copies of pAW RNA. Slope of curve used to determine quantity of pAW RNA in each of the samples. R2 value of 0.997 (>0.95) indicates good linearity. FIG. 2B is an Amplification plot showing amplification curves of pAW standards. Cycle threshold sets at 0.2 indicated by the thick horizontal line. The cycle number (Ct) value for each pAW standard used to determine the line in FIG. 2A. FIG. 2C is an Amplification plot of pAW in samples of positive control VQA 0, 200, 1500, and 15,000. The cycle numbers, a cross point with the threshold 0.2 (thick horizontal line) for each VQA was used to determine its quantity. All pAW is included at the same amount in each sample, showing within 2 cycles of each other and validates RNA extraction successful. FIG. 2D is an Amplification plot of pAW in samples of the WHO International HIV-1 Standard tested. The cycle numbers, a cross point with the threshold 0.2 (thick horizontal line) for each standard was used to determine its quantity. Again closeness of each curve validates RNA extraction process.

FIG. 3A is a Graph of Standard Curve of HIV RNA Assay Standards from 4E0 to 4E5 used in assay. R2 value of 0.996 validates linearity of curve. FIG. 3B is an Amplification plot of HIV RNA standards, 4E0-4E5, run in duplicate. FIG. 3C is an Amplification plot of VQA positive controls 0, 200, and 1500 run in duplicate in assay. Sample with 0 copies does not present an amplification curve. FIG. 3D is an Amplification plot of all tested samples of 2, 3, 4, 5, 10, and 20 copies/mL derived from the WHO International Standard, showing quantitation of low levels of HIV-1 RNA.

FIG. 4A is a Standard Curve of pAW standards, slope equation used to determine pAW quantities in each sample. R2 value is 0.998 (>0.95). FIG. 4B is an Amplification plot showing amplification curves of pAW standards. Cycle threshold set at 0.2. FIG. 4C is an Amplification plot of pAW in samples of VQA 0, 200, 1500. All pAW curves show the same amount pAW in each sample, within 2 cycles of each other, which validates RNA extraction process successful. FIG. 4D is an Amplification plot of pAW in samples of WHO International HIV-1 Standard tested. The closeness of all curves to each other validates RNA extraction process.

FIG. 5A is a Standard Curve of the HCV RNA Assay Standards 4, 40, 400, 4E3, 4E4, 4E5, 4E6, 4E7 copies used in the HIV-1 Ultra PCR for determining quantities of samples. Copies/mL (X axis) plotted against Cycle Number (Ct) determines slope of line used to determine sample quantity. R2 value of 0.997 indicates a high degree of linearity of the standards over this range. FIG. 5B is an Amplification plot of the AcroMetrix® HCV Standard of HCV RNA with nominal quantities of 4E0, 4E1, 4E2, 4E3, 4E4, 4E5, 4E6, 4E7 copies. Each dilution is tested in duplicate. The cycle numbers, a cross point with the threshold 0.2 (thick horizontal line) for each sample was used to determine its quantity. FIG. 5C is a Standard curve of pAW RNA using 5E2, 5E3, and 5E4 copies of pAW RNA. Slope of curve used to determine quantity of pAW RNA in each of the samples. R2 value of 0.99 (>0.95) indicates good linearity.

FIG. 6A is a Standard Curve of the HCV RNA Assay Standards 4, 40, 400, 4E3, 4E4, 4E5, 4E6, 4E7 copies used in the HIV-1 Ultra PCR for determining quantities of samples. Copies/mL (X axis) plotted against Cycle Number (Ct) determines slope of line used to determine sample quantity. R2 value of 0.990 indicates a high degree of linearity of the standards over this range. FIG. 6B is an Amplification plot of the HCV RNA Assay standards used to determine the standard curve and evaluate the exponential growth of signal during PCR. Each standard is tested in duplicate, and the thick horizontal line is the threshold set to determine the Ct value for all standards used to determine the line in FIG. 6A. FIG. 6C is an Amplification plot of the AcroMetrix® HCV Standard of HCV RNA with nominal quantities of 4E0, 4E1, 4E2, 4E3, 4E4, 4E5, 4E6, 4E7 copies. Each dilution is tested in duplicate. The cycle numbers, a cross point with the threshold 0.2 (thick horizontal line) for each sample was used to determine its quantity. FIG. 6D is an Amplification plot of Internal control pAW in samples of AcroMetrix® HCV standards at 4E0, 4E1, 4E2, 4E3, 4E4, 4E5, 4E6, 4E7 copies. All pAW is included at the same amount in each sample, showing within 2 cycles of each other and validates RNA extraction successful. Based on AcroMetrix® HCV positive controls as standard curve is used to quantify the in house HCV RNA Standard.

DETAILED DESCRIPTION OF THE INVENTION

Figure 1A:
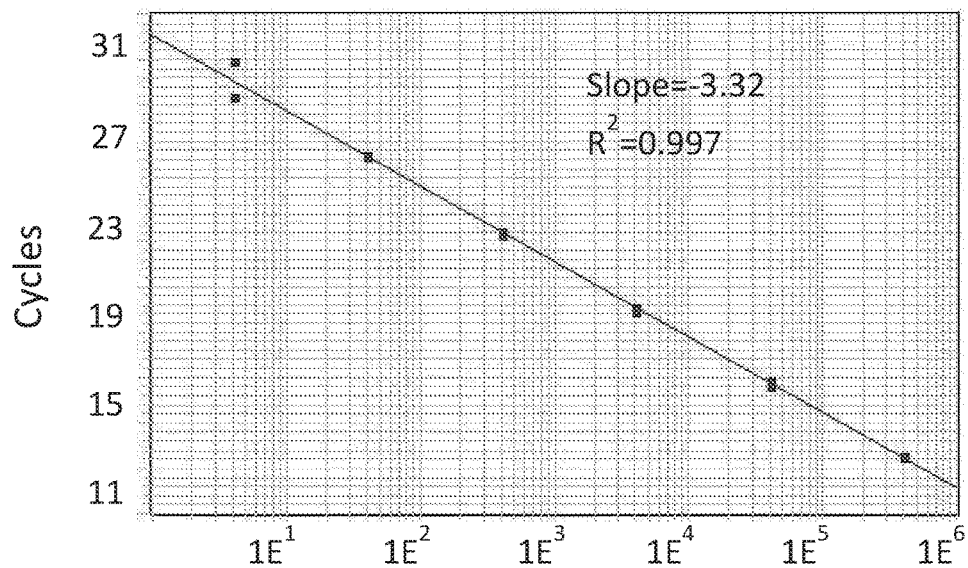
FIGS. 1A-1D. Quantitative detection of the World Health Organization (WHO) International Standard of HIV-1 RNA (Version 3.0) and NIH Virology Quality Assurance (VQA) Standard of HIV-1 RNA.

The invention provides new methods for detection of HIV-1 RNA and DNA, and HCV RNA. These assays are more sensitive than commercially available assays. Because of the high diversity of HIV-1 and HCV sequences worldwide, hundreds of primers and probes were designed and tested by real experiments, and the primers and probes that worked for all subtypes of HIV-1 M group and O group, as well as all HCV subtypes, were identified and selected. To perform the 3 rounds of PCR in a single tube, the real time PCR protocol was modified, including 3 pairs of primers, compositions of PCR reaction buffer and cycle conditions. The integrated 3 rounds of Ultrasensitive PCR (Ultra PCR) increased assay sensitivity. The detection limit of the HIV-1 RNA and HCV RNA Ultra PCR is 4 copies/ml blood plasma whereas the detection limit of the best commercially available assays is 20-50 copies/ml blood plasma. The detection limit of the HIV DNA Ultra PCR is 4 copies/million cells, whereas the conventional real time PCR is over 100 copies/million cells. The integrated 3 rounds of PCR started with amplification cycles with higher annealing temperature, which increase the specific binding of primers with targeted sequences of the templates. In addition, 3 rounds of PCR provide three steps of selection of the targeted genes during PCR reaction, improving the assay specificity. This is the first provision of a single tube 3 round real time PCR assay for HIV-1/HCV and all HIV-1/HCV subtypes. Also provided are new assay standards and internal controls specifically for HIV-1 and HCV Ultra PCR.

Viral load is considered a major biomarker for therapeutic efficacy and infection cure. However, currently available commercial products of viral load detection kits are unable to fulfill this task because of limitation of sensitivity. The HIV-1 and HCV Ultra PCR described herein address this health care need due to the significantly higher sensitivity. In addition, HIV-1 and HCV Ultra PCR provide a diagnostic tool with higher sensitivity and specificity than those commercially available.

Definitions

All scientific and technical terms used in this application have meanings commonly used in the art unless otherwise specified. As used in this application, the following words or phrases have the meanings specified.

The term "nucleic acid" or "polynucleotide" or "oligonucleotide" refers to a sequence of nucleotides, a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

The term "primer," as used herein, means an oligonucleotide designed to flank a region of DNA to be amplified. In a primer pair, one primer is complementary to nucleotides present on the sense strand at one end of a polynucleotide fragment to be amplified and another primer is complementary to nucleotides present on the antisense strand at the other end of the polynucleotide fragment to be amplified. A primer can have at least about 11 nucleotides, and preferably, at least about 16 nucleotides and no more than about 35 nucleotides. Typically, a primer has at least about 80% sequence identity, preferably at least about 90% sequence identity with a target polynucleotide to which the primer hybridizes.

As used herein, the term "probe" refers to an oligonucleotide, naturally or synthetically produced, via recombinant methods or by PCR amplification, that hybridizes to at least part of another oligonucleotide of interest. A probe can be single-stranded or double-stranded.

As used herein, the term "active fragment" refers to a substantial portion of an oligonucleotide that is capable of performing the same function of specifically hybridizing to a target polynucleotide.

As used herein, "hybridizes," "hybridizing," and "hybridization" means that the oligonucleotide forms a noncovalent interaction with the target DNA molecule under standard conditions. Standard hybridizing conditions are those conditions that allow an oligonucleotide probe or primer to hybridize to a target DNA molecule. Such conditions are readily determined for an oligonucleotide probe or primer and the target DNA molecule using techniques well known to those skilled in the art. The nucleotide sequence of a target polynucleotide is generally a sequence complementary to the oligonucleotide primer or probe. The hybridizing oligonucleotide may contain nonhybridizing nucleotides that do not interfere with forming the noncovalent interaction. The nonhybridizing nucleotides of an oligonucleotide primer or probe may be located at an end of the hybridizing oligonucleotide or within the hybridizing oligonucleotide. Thus, an oligonucleotide probe or primer does not have to be complementary to all the nucleotides of the target sequence as long as there is hybridization under standard hybridization conditions.

The term "complement" and "complementary" as used herein, refers to the ability of two DNA molecules to base pair with each other, where an adenine on one DNA molecule will base pair to a guanine on a second DNA molecule and a cytosine on one DNA molecule will base pair to a thymine on a second DNA molecule. Two DNA molecules are complementary to each other when a nucleotide sequence in one DNA molecule can base pair with a nucleotide sequence in a second DNA molecule. For instance, the two DNA molecules 5'-ATGC and 5'-GCAT are complementary, and the complement of the DNA molecule 5'-ATGC is 5'-GCAT. The term complement and complementary also encompasses two DNA molecules where one DNA molecule contains at least one nucleotide that will not base pair to at least one nucleotide present on a second DNA molecule. For instance, the third nucleotide of each of the two DNA molecules 5'-ATTGC and 5'-GCTAT will not base pair, but these two DNA molecules are complementary as defined herein. Typically, two DNA molecules are complementary if they hybridize under the standard conditions referred to above. Typically, two DNA molecules are complementary if they have at least about 80% sequence identity, preferably at least about 90% sequence identity.

As used herein, "a" or "an" means at least one, unless clearly indicated otherwise.

As used herein, to "prevent" or "protect against" a condition or disease means to hinder, reduce or delay the onset or progression of the condition or disease.

As used herein, the term "isolated" means that a naturally occurring DNA fragment, DNA molecule, coding sequence, or oligonucleotide is removed from its natural environment, or is a synthetic molecule or cloned product. Preferably, the DNA fragment, DNA molecule, coding sequence, or oligonucleotide is purified, i.e., essentially free from any other DNA fragment. DNA molecule, coding sequence, or oligonucleotide and associated cellular products or other impurities.

Primers and Probes

Primers are useful in the synthesis of copies of a target sequence of HIV or HCV, whereas corresponding probes hybridize with amplification products of the primed synthesis. The nucleic acid sequence to be amplified can be referred to as the template. The nucleotides of a nucleic acid sequence to which a primer is complementary is referred to as a target sequence. The target sequence may be DNA or RNA. With an RNA target sequence, cDNA can be transcribed from the RNA to provide a template DNA for amplification using known techniques. A primer may serve as a starting point for a polymerase which, in the presence of the necessary materials, synthesizes a DNA molecule that is complementary to the template DNA.

Probes are useful in the detection, identification and isolation of particular nucleic acid sequences. In a typical embodiment, a probe used in the present invention is labeled with a reporter molecule, so that it is detectable in a direct or indirect detection system. Examples of direct detection systems include, but are not limited to, fluorescent, radioactive, and luminescent systems. Indirect detection systems include the use of specific binding partners, which may be used in combination with a directly detectable label to which it is attached. In one embodiment, the probe is a probe represented by SEQ ID NOs:7, 13-15 (HIV-1). In one embodiment, the probe is a probe represented by SEQ ID NOs:22, 25, or 26 (HCV).

In one preferred embodiment, the probe of the present invention can be a probe having fluorescent molecules at its 5' and 3' ends. In one embodiment, the probe contains a fluorescent reporter and a quencher at its 5' and 3' ends, respectively, in which they can show interference with each other. Therefore, when the probes bind to 5'-UTR in the sample, the generation of fluorescent signals is restricted. Upon performing polymerase chain reaction, the probe is decomposed, and the fluorescent reporter at the 5' end is released away from the quencher at the 3' end, thereby generating fluorescent signals. The presence of HIV-1 or HCV in the sample can be detected by the fluorescent signals.

Fluorescent molecules that are typically known to those skilled in the art can be used to label the probe at the 5' end. Representative examples of such molecules include, but are not limited to, 6-carboxyfluorescein (FAM), hexachloro-6-carboxyfluorescein (HEX), tetrachloro-6-carboxyfluorescein. Cyanine-5 (Cy5), but are not limited thereto. Fluorescent molecules that are typically known to those skilled in the art can be used to label the probe at the 3' end. Representative examples of such molecules include, but are not limited to, 6-carboxytetramethyl-rhodamine (TAMRA) and BHQ-1, 2, 3 (black hole quencher-1, 2, 3).

TABLE 1

HIV-1 Primers and Probe

| Set #1 Primers | 5'-3' |
|---|---|
| SEQ ID NO: 1: | TCTGGCTAACTAGGGAACCCACTGCT |
| SEQ ID NO: 2: | TGCGCGCTTCAAGCCGAGTCCTGCGT |
| SEQ ID NO: 3: | AGGGAACCCACTGCTTAAGCCTCAATAAAGCT |
| SEQ ID NO: 4: | AGCAAGCCGAGTCCTGCGTCGAGA |
| SEQ ID NO: 5: | AGCCTCAATAAAGCTTGCCT |
| SEQ ID NO: 6: | CCGCCACTGCTAGAGATTTTCCA |
| Probe | |
| SEQ ID NO: 7: | TCTGGTAACTAGAGATCCCT |
| Set #2 Primers | 5'-3' |
| SEQ ID NO: 8: | GGTTAGACCAGATCTGAGCCTGGGAGCT |
| SEQ ID NO: 2: | TGCGCGCTTCAAGCCGAGTCCTGCGT |
| SEQ ID NO: 9: | GGAACCCACTGCTTAAGCCTCAATAAAGCTTGC |
| SEQ ID NO: 10: | TGTTCGGGCGCCACTGCTAGAGA |
| SEQ ID NO: 11: | AAGCCTCAATAAAGCTTGCCTTGA |
| SEQ ID NO: 12: | AGGGTCTGAGGGATCTCTAGTTACCAGAG |
| Probe | |
| SEQ ID NO: 13: Or | TTCAAGTAGTGTGTGCCC |
| SEQ ID NO: 14: Or | AGTAGTGTGTGCCCGTCT |
| SEQ ID NO: 15: | TAGTGTGTGCCCGTCTGT |

TABLE 2

HCV Primers and Probe

| Set #1 Primers | 5'-3' |
|---|---|
| SEQ ID NO: 16: | CCCCTCCCGGGAGAGCCATAGT |
| SEQ ID NO: 17: | GCACCCTATCAGGCAGTACCACAAGGCCTTT |
| SEQ ID NO: 18: | CCCCCCTCCCGGGAGAGCCATAGTGG |
| SEQ ID NO: 19: | CTCGCGGGGCACGCCCAAAT |
| SEQ ID NO: 20: | TCCCGGGAGAGCCATAGT |
| SEQ ID NO: 21: | GGGTTTATCCAAGAAAGGACCC |
| Probe | |
| SEQ ID NO: 22: | 6FAM-TGCGGAACCGGTGAGT-MGB |
| Set #2 Primers | 5'-3' |
| SEQ ID NO: 16: | CCCCTCCCGGGAGAGCCATAGT |
| SEQ ID NO: 23: | TCAGGCAGTACCACAAGGCCTTTCGC |
| SEQ ID NO: 18: | CCCCCCTCCCGGGAGAGCCATAGTGG |

TABLE 2-continued

HCV Primers and Probe

| SEQ ID NO: 24: | GCGGGGGCACGCCCAAAT |
| --- | --- |
| SEQ ID NO: 20: | TCCCGGGAGAGCCATAGT |
| SEQ ID NO: 21: | GGGTTTATCCAAGAAAGGACCC |

Probe

| SEQ ID NO: 25: Or | FAM-TCTGCGGAACCGGTGA-MGB |
| --- | --- |
| SEQ ID NO: 26: | FAM-CTGCGGAACCGGTGAG-MGB |

Additional HCV reverse primers

| SEQ ID NO: 27: | CCTATCAGGCAGTACCACAAGG |
| --- | --- |
| SEQ ID NO: 28: | AGTACCACAAGGCCTTTCGC |
| SEQ ID NO: 29: | CACCCTATCAGGCAGTACCAC |
| SEQ ID NO: 30: | TCAGGCAGTACCACAAGGC |

Primers and Probe Design and Selection

A nucleotide acid sequence alignment was set up that contained HIV-1 sequences present in GenBank and the Los Alamos National Laboratory database (HIV-1 2012). Primers and probe binding in conserved domains were designed by analyses of sequences including alignment and further justified by the Primer Express software (Life Technologies) and related programs. Due to the extremely high divergence of HIV-1 and HCV worldwide, hundreds of primers and probes were initially designed and further tested by real experiments, leading to selection and identification of the primers and probes that worked for all subtypes of HIV-1 M group and O group (Table 1), as well as all HCV subtypes (Table 2). To perform 3 rounds of PCR in one tube, designed 3 pairs of primers were designed: the first pair of primers with annealing temperature at 65-71° C., second pair with annealing temperature at 60-64° C., and third pair with annealing temperature at 50-55° C. The first round PCR is designed to perform at high annealing temperature, which increases the specificity of the initial 5-10 cycles of PCR. The second round of PCR is designed to further enhance the specificity of PCR and produce enough PCR products for third round of PCR, which is designed to maximally amplify the target and increase the sensitivity. The combination of 3 rounds of PCR thus increases the sensitivity and specificity of PCR.

HIV-1 and HCV RNA Extraction 1-2 ml of blood plasma is placed in a 2.0 mL Sarstedt tube and centrifuged for 1 to 2 hours at 23,000 g at 4° C. After centrifugation, the supernatant is removed. To the pellet is added 600 microliters of a lysis buffer (5.75M Guanidinium isothiocyanate, 190 mM dithiothreitol, 25 mM Tris-HCl) to which glycogen (10 mg/mL) and a known amount of pAW 109 internal RNA control (~20.000 copies, Life Technologies) have been added. After vortexing and a 15-minute incubation at room temperature, 600 µL of isopropanol are added to each tube, mixed well, and then centrifuged for 20 minutes at 14,000 rpm. The supernatant is carefully aspirated to avoid pellet disruption and 1 mL of 70% ethanol is added, then gently vortexed for 10 seconds and centrifuged at 14,000 rpm for 5 minutes. The supernatant is aspirated out without disturbing the pellet and air-dried for 8-10 minutes. 50 µl of AE buffer are added to the dried pellet and vortexed for 10 seconds to thoroughly dissolve the RNA. The extracted RNA samples are added to the RT-PCR or stored at −70 C°.

HIV-1 RNA Assay standards

To create HIV RNA standards, the LTR region of the HIV-1 gene was PCR amplified from NL4-3 plasmid with primers SEQ ID NO: 8 and SEQ ID NO: 2 to amplify a 235 bp product and cloned into pCR2.1 TOPO cloning vector (Life Technologies) according to the manufacturer's instructions. The cloned plasmids containing pNL4-3 of HIV LTR region were then purified with QIAGEN Minipreps DNA kit (QIAGEN). Restriction enzyme EcoR1 digestion and DNA sequencing determined the presence and orientation of LTR/pNL4-3 insert. The purified plasmids containing HIV LTR were linearized by restriction enzyme SpeI digestion and purified by phenol-chloroform extraction and alcohol precipitation. These cloned plasmids containing HIV LTR were then transcribed into specific RNA using MEGAshortscript kit (Life Technologies). HIV LTR RNA was treated with Turbo DNase I (Life Technology) and purified with phenol-chloroform extraction and alcohol precipitation. The purified HIV-1 RNA transcript was analyzed with Agilent 2100 Bioanalyzer (Agilent Technologies). To determine the concentration and quantity of the RNA standard, a standard calculation based on its Absorbance 260 and molecular weight of the RNA standard was performed. These quantities were validated by running dilution curves against the known quantities of HIV-1 plasma samples. Running dilution curves against the known quantities of HIV-1 plasma samples validated these quantities. Dilutions of the HIV-1 RNA were made to produce a standard curve equivalent to 2E5, 2E4, 2E3, 2E2 and 2E1 copies/reaction. HIV-1 RNA standards were used as standard control to measure quantitatively HIV-1 RNA in samples, including but not limited to, plasma and serum by the real-time RT-PCR in the subsequent experiments.

HIV-1 DNA Assay Standards

ACH-2 is a cell line that was infected with a full-length single integrated copy of HIV-1 LAV strain. It constantly produces only one integrated proviral copy per cell. ACH-2 is obtained from NIH AIDS Reagent Program. Human genomic DNA was purchased from Promega (Promega Corporation, Madison, Wis. 53711). ACH-2 was cultured in cell suspension with RPMI 1640 supplemented with 10 mM HEPES, 2 mM L-glutamine, 90%; heat inactivated fetal bovine serum, 10%. The cells were harvested for DNA extraction with Qiagen DNA extraction kit. The ACH-2 DNA was measured with Nano spectrophotometer, and its concentration was calculated based on its OD260, which was used to generate quantification proviral DNA standards.

HCV RNA Assay Standards

To prepare HCV RNA standard, RT-PCR was performed with the primer pair of HCV-F38 CACTCCCCTGTGAG-GAACTACTGTCT (SEQ ID NO: 31) and HCV-R343 TGGTGCACGGTCTACGAGACCTCCC (SEQ ID NO: 32) to generate from HCV plasma panel (genotype 1b) purchased from AcroMetrix/Applied Biosystems/Life Technologies) and Armored RNA Quant Hepatitis C Viruses (genotype2b) purchased from Asuragen Inc. HCV 5'UTG of 306 bp of PCR product were amplified by RT-PCR with the primer pair of SEQ ID NO: 31/SEQ ID NO: 32, which was then cloned into pCR2.1 Vector using the TOPO TA Cloning Kit (Life Technologies). The cloned plasmids containing of HCV 5'UTG region were then purified with QIAGEN Minipreps DNA kit (QIAGEN). Restriction enzymes of EcoRV and BstXI double digestion and DNA sequencing determined the presence and orientation of HCV 5'UTG insert.

The purified plasmids containing HCV 5'UTG were linearized by restriction enzyme Hind III digestion and purified by phenol-chloroform extraction and alcohol precipitation. These cloned plasmids containing HCV 5'UTG were then transcribed into specific RNA using MEGAshortscript kit (Life Technologies). HCV 5'UTG RNA was treated with Turbo DNase I (Life Technology) and purified with phenol-chloroform extraction and alcohol precipitation. The purified 5'UTG transcript was analyzed with Agilent 2100 Bioanalyzer (Agilent Technologies). The concentration and quantitation of purified RNA was determined by spectrophotometer and was used as a standard control to measure quantitatively HCV RNA in plasma and serum by real-time RT-PCR with the primers and probes as shown in Table 2 in the subsequent experiments. This in-house standard was tested in parallel with the one of highest HCV plasma panel member that was diluted into 5600, 560, 56, 5.6, 1.9 IU/RXN or 14000, 1400, 140, 14 and 1.41 U/ml. HCV RNA standard were made to produce a standard curve equivalent to 1E8, 1E7, 1E6, 1E5, 1E4, 1E3, 1E2, 1E1, 1E0 IU/reaction.

HIV-1 and HCV Assay Controls

Internal control standards were created, using pAW109 RNA. A three-point standard curve was made from dilutions of the stock to 50,000, 5,000 and 500 copies/reaction.

A single separate PCR reaction well was used to determine extraction quality. Five microliters of RNA were added to 20 ml of master mix. The 5' primer GCCTGGGTTCCCTGTTCC (SEQ ID NO: 33) and the 3' primer CGACGTACCCCTGACATGG (SEQ ID NO: 34) were each used at a final concentration of 1,080 nM, and the probe VIC-CCAGGCCAATGTCTCACCAAGCTCTG (SEQ ID NO: 35)-minor groove binder (MGB), nonfluorescent quencher was used at a final concentration of 480 nM. The HIV and internal control pAW 109 RNA primer sequencer reactions were performed under identical conditions. The amplification reaction was carried out in a real time PCR instrument with the following cycles: 50° C. for 10 min, 95° C. for 10 min, then 5-10 cycles of 95° C. for 15 s, 65-71° C. for 15 s and 72'C for 20 s, 10-20 cycles of 95° C. for 15 s. 60-64° C. for 15 s and 72'C for 20 s, and 30-40 cycles of 95° C. for 15 s, 50-55° C. for 15 s and 72° C. for 20 s for a total of 55 cycles. Analysis was performed with the software of the PCR companies.

HIV known quantity controls from Virology Quality Assurance laboratory, (Rush University, NIH DAIDS VQA Program) 0, 150, 1500, and 15,000 copies/ml were included in each set up. VQAs were parallel extracted with HIV patient sample, RT-PCR and its analysis to determine if VQA are within their lot range. That would determine if the assay/reaction is successful.

Negative template control was also included.

HIV-1 and HCV Ultra PCR

For HIV-1 and HCV detection and quantification, the Ultra PCR was performed with 2-5 units of Reverse Transcriptase, such as efficient ArrayScript™ Reverse Transcriptase that produces high cDNA yields, and 3-8 units of Polymerase, such as AmpliTaq Gold® polymerase (Life Technologies), 1-10 nM of each of the first round oligonucleotide primers, 10-100 nM of each of second round PCR oligonucleotide primers including second round PCR primers, 0.2-1 µM of third round PCR primers and 0.1-0.8 µM of probe (see Tables 1 and 2), 0.2-0.8 mM deoxynucleotide triphosphates (dNTP), 2-8 mM $MgCl_2$; 10-20 µl of HIV-1 or HCV RNA extracted from patient plasma samples and 1×RT-PCR enzyme mix and 1-2 µl of RNase inhibitor (Life Technologies). The HIV-1 and HCV Ultra PCR was performed as follows: reverse transcription at 45° C. for 10 min and activation at 95° C. for 10 min followed by 5-10 cycles of 95° C. for 15 sec, 65-71° C. for 15 sec (first round PCR) and 72° C. for 20 sec, 10-20 cycles of 95° C. for 15 sec, 60-64° C. for 15 sec (second round PCR) and 72° C. for 20 sec, and real time PCR for 30-40 cycles at 95° C. for 15 sec. 50-55° C. for 15 sec and 72° C. for 20 sec (third round PCR). Quantification standard, internal control pAW109 RNA standard, HIV-1 and HCV positive control consisted 0, 150, 1,500 and 150,000 copies/mi of HIV-1, as well as NTC were run in duplicate.

The HIV-1 and HCV Ultra PCR were carried out using a Real Time PCR Detection System. Data were analyzed with Sequence Detection System (SDS) software 2.2.2 (Applied Biosystems. Foster City, Calif.). The baseline was automatically set up, and the threshold was set at 0.20 for all detectors. The Ct values of unknown samples were plotted against quantification standard, and the number of HIV-1 RNA copies per ml was quantified. The criteria for an acceptable run are with no contamination, standard curve $R^2>=95\%$, duplicate within 2 Ct of each other, VQA within lot range and internal control pAW present close to 400-2000 copies/run.

Kits

The invention provides kits comprising a set of oligonucleotides as described herein, and optionally, one or more suitable containers containing oligonucleotides of the invention. Kits of the invention optionally further comprise an enzyme having polymerase activity, deoxynucleotide triphosphates (dNTP), and an enzyme having reverse transcriptase activity. Kits can include one or more primer pairs, and in some embodiments, at least one corresponding probe of the invention, as well as internal control primer and probe sequences. The kit can optionally include a buffer. In one embodiment, the buffer is 1×RT-PCR buffer. In one embodiment, the kit includes materials to perform the amplification and detection of HIV and/or HCV in a single reaction tube.

In one embodiment, a composition or kit of the invention further comprises one or more, or each of the following: 2-5 units of a Reverse Transcriptase. 3-8 units of a Polymerase, 1-10 nM of each of the first round oligonucleotide primers, 10-100 nM of each of second round PCR oligonucleotide primers including second round PCR primers, 0.2-1 µM of third round PCR primers and 0.1-0.8 µM of probe (see Tables 1 and 2), 0.2-0.8 mM dNTP, 2-8 mM $MgCl_2$; 10-20 µl of HIV-1 or HCV RNA extracted from patient plasma samples, and 1-2 µl of RNase inhibitor (Life Technologies). A unit of AgPath-ID™ one step RT-PCR enzyme for 100 reactions of 25 µL, contains: 1375 µL 2×RT-PCR Buffer, 110 µL 25×RT-PCR Enzyme Mix, 190 µL Detection Enhancer, and 1.75 mL Nuclease-free Water. In one embodiment, the composition or kit comprises 1-10 nM of each of the first round oligonucleotide primers, 10-100 nM of each of second round PCR oligonucleotide primers including second round PCR primers, 0.2-1 µM of third round PCR primers and 0.1-0.8 µM of probe, wherein the primers and probe(s) are selected from Tables 1 and 2. In one embodiment, the composition or kit comprises 0.2-0.8 mM dNTP, and 2-8 mM $MgCl_2$.

Methods of the Invention

The invention provides methods for detecting an RNA virus in a sample. The methods provide an ultrasensitive polymerase chain reaction (Ultra PCR) that can be used to detect all subtypes of HIV-1 M group and O group, and all HCV subtypes. Three rounds of PCR can be integrated for increased assay sensitivity and specificity. The method is capable of detecting less than 10 copies/mi blood plasma of HIV-1 RNA or HCV RNA, and less than 10 copies/million cells of HIV DNA. The method features a detection limit of 4 copies/ml blood plasma of HIV-1 RNA or HCV RNA, and 4 copies/million cells of HIV DNA. Specificity of the assay is enhanced both via higher annealing temperature and via three steps of selection of the targeted genes during the 3 rounds of PCR and probe hybridization. Moreover, the 3 round real time PCR assay can be performed in a single tube. The invention additionally provides assay standards and internal controls specifically for HIV-1 and HCV Ultra PCR.

In one embodiment, the method comprises isolating RNA in a sample, submitting the isolated RNA to reverse transcription PCR, contacting the resulting reverse transcription PCR product with a set of primers as described herein, and submitting the resulting mixture to one or more nucleic acid amplification reactions. The invention also provides a method for detecting HIV-1 in a sample. In one embodiment, the method comprises isolating RNA in a sample, submitting the isolated RNA to reverse transcription PCR, contacting the resulting reverse transcription PCR product with a set of primers as described in Table 1, and submitting the resulting mixture to one or more nucleic acid amplification reactions. In one embodiment, the invention provides a method for detecting HIV-1 in a sample, wherein the method comprises isolating RNA in a sample, submitting the isolated RNA to reverse transcription PCR, contacting the resulting reverse transcription PCR product with a set of outer primers, and submitting the resulting mixture to a first nucleic acid amplification reaction, wherein the set of primers comprises a combination of oligonucleotides as defined in Table 1. Optionally, the method further comprises contacting a product from the first nucleic acid amplification reaction with a set of middle primers and submitting the resulting mixture to a second nucleic acid amplification reaction. The method can further comprise contacting a product from the second nucleic acid amplification reaction with a set of inner primers and submitting the resulting mixture to a third nucleic acid amplification reaction. The method optionally further comprises contacting a product from the third nucleic amplification reaction with the probe for quantitation by real time PCR.

The invention additionally provides a method for detecting HCV in a sample comprising: isolating RNA in a sample, submitting the isolated RNA to reverse transcription PCR, contacting the resulting reverse transcription PCR product with a set of primers as described in Table 2, and submitting the resulting mixture to one or more nucleic acid amplification reactions. In one embodiment, the invention provides a method for detecting HCV in a sample comprising: isolating RNA in a sample, submitting the isolated RNA to reverse transcription PCR, contacting the resulting reverse transcription PCR product with a set of outer primers, and submitting the resulting mixture to a first nucleic acid amplification reaction, wherein the set of primers comprises a combination of oligonucleotides as defined in Table 2. The method optionally further comprises contacting a product from the first nucleic acid amplification reaction with a set of middle primers and submitting the resulting mixture to a second nucleic acid amplification reaction. Optionally, the method further comprising contacting a product from the second nucleic acid amplification reaction with a set of inner primers and submitting the resulting mixture to a third nucleic acid amplification reaction. The method can further comprise contacting a product from the third nucleic amplification reaction with the probe for quantitation by real time PCR.

The invention further provides a method for detecting HCV in a sample comprising: isolating RNA in a sample, submitting the isolated RNA to reverse transcription PCR, contacting the resulting reverse transcription PCR product with a set of outer primers, and submitting the resulting mixture to a first nucleic acid amplification reaction, wherein the primers comprises a combination of oligonucleotides as defined in Table 2. In one embodiment, the method further comprises contacting a product from the first nucleic acid amplification reaction with a set of middle primers and submitting the resulting mixture to a second nucleic acid amplification reaction. The method can further comprise contacting a product from the second nucleic acid amplification reaction with a set of inner primers and submitting the resulting mixture to a third nucleic acid amplification reaction. In one embodiment, the method further comprises contacting a product from the third nucleic amplification reaction with the probe for quantitation by real time PCR.

In the methods described herein, the first nucleic acid amplification reaction is typically performed at a temperature of about 65-71'C, the second nucleic acid amplification reaction is typically performed at a temperature of about 60-64° C., and the third nucleic acid amplification reaction is typically performed at a temperature of about 50-55° C. Optionally, the method is carried out in a single tube.

In one embodiment, the method is performed with about 1-10 nM of each of the first round primers, about 10-100 nM of each of the second round primers, about 0.1-1 µM of the third round primers, and about 0.1-0.8 µM of the corresponding probe (see Tables 1 and 2). In one embodiment, the sample contains about 10 µl of HIV-1 or HCV RNA. Typically, the RNA is extracted from patient plasma samples. In one embodiment, the HIV-1 or HCV RNA is provided with 1×RT-PCR enzyme mix and 1 µl of RNase inhibitor (Life Technologies).

In some embodiments, the RNA virus is HIV and/or HCV. In some embodiments, the sample contains less than 15 copies, less than 10 copies, or less than 5 copies of the RNA virus. In one embodiment, the HIV is HIV-1. Examples of HIV-1 include, but are not limited to, HIV-1 subtypes of the M and O groups.

The invention further provides a method for monitoring the efficacy of anti-retroviral treatment in a subject infected with HIV or HCV. In one embodiment, the method comprises subjecting a sample obtained from the subject to a method for detecting an RNA virus as described herein; and determining whether the sample contains fewer copies of the virus per milliliter than a predetermined threshold. A reduction in copies of the virus per milliliter sample is indicative of effective anti-retroviral treatment. In one embodiment, the predetermined threshold is an amount detected in a prior sample obtained from the subject at a previous time point. In one embodiment, the predetermined threshold is 5 copies of virus per milliliter sample. In one embodiment, the threshold is 4 copies of virus per milliliter sample.

The invention additionally provides a method for detecting acute HIV-1 infection in a subject. In one embodiment, the method comprises subjecting a sample obtained from the subject to a method of detecting HIV described herein; and determining whether the sample contains a detectable amount of HIV-1 DNA or RNA. The presence of a detectable amount of HIV-1 DNA or RNA is indicative of acute HIV-1 infection. In one embodiment, the subject is known or suspected to have recent exposure to HIV-1 under conditions that risk viral transmission. In another embodiment, the subject has experienced symptoms indicative of acute HIV-1 infection. The method allows for early detection of HIV infection, which allows for prompt initiation of antiretroviral treatment and improved clinical outcomes.

The invention also provides a method for detecting acute early HCV infection in a subject. In one embodiment, the method comprises subjecting a sample obtained from the subject to a method of detecting HCV as described herein; and determining whether the sample contains a detectable amount of HCV RNA. The presence of a detectable amount of HCV RNA is indicative of acute early HCV infection. In one embodiment, the subject is known or suspected to have recent exposure to HCV under conditions that risk viral transmission. In another embodiment, the subject has experienced symptoms indicative of acute HCV infection, such as elevated aminotransferase levels. The method allows for early detection of HCV infection, which allows for prompt initiation of treatment and improved clinical outcomes. In some embodiments, HCV RNA is monitored for possible spontaneous clearance prior to deciding whether to initiate treatment.

For use in the methods described herein, representative examples of the sample include, but are not limited to, blood, plasma or serum, saliva, urine, cerebral spinal fluid, milk, cervical secretions, semen, tissue, cell cultures, and other bodily fluids or tissue specimens.

EXAMPLES

The following examples are presented to illustrate the present invention and to assist one of ordinary skill in making and using the same. The examples are not intended in any way to otherwise limit the scope of the invention.

Example 1: Preparation of HIV-1 and HCV Primers and Probes

Figure 1B:
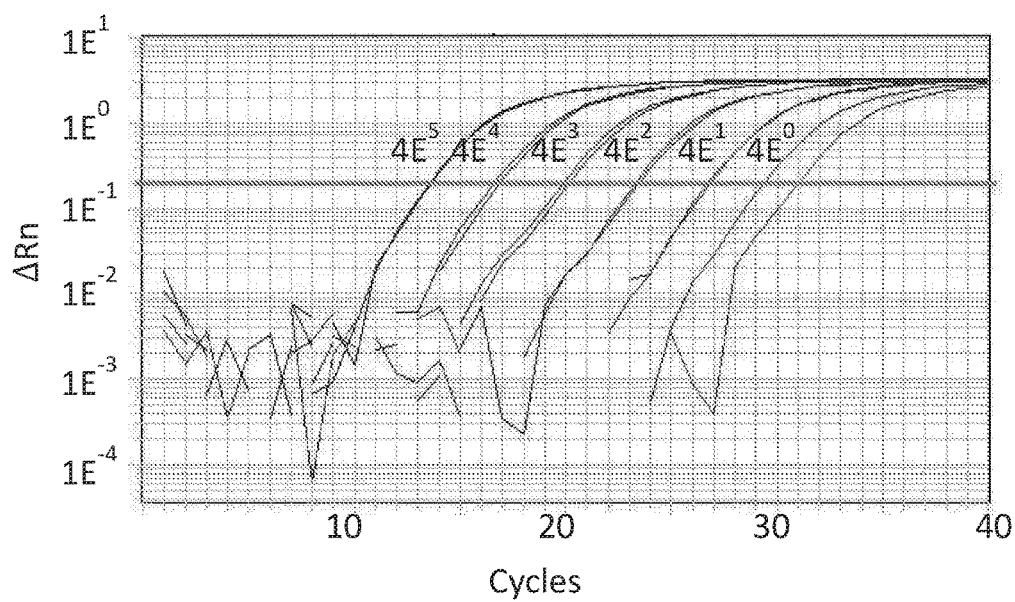
Figure 1C:
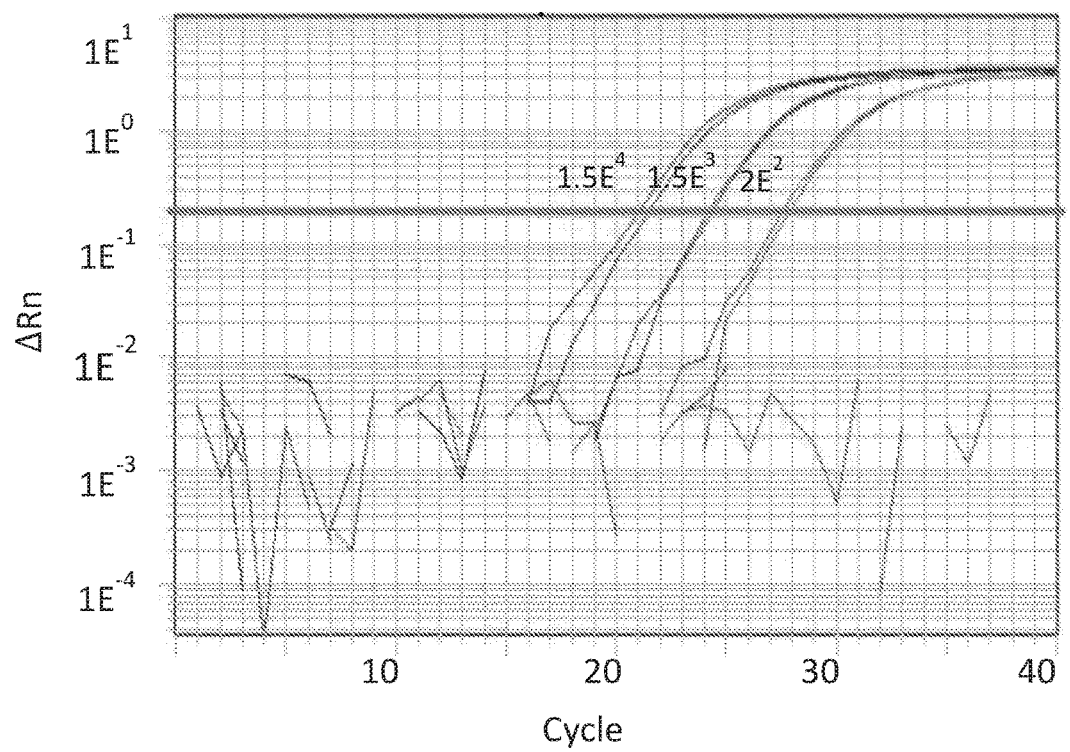
Figure 1D:
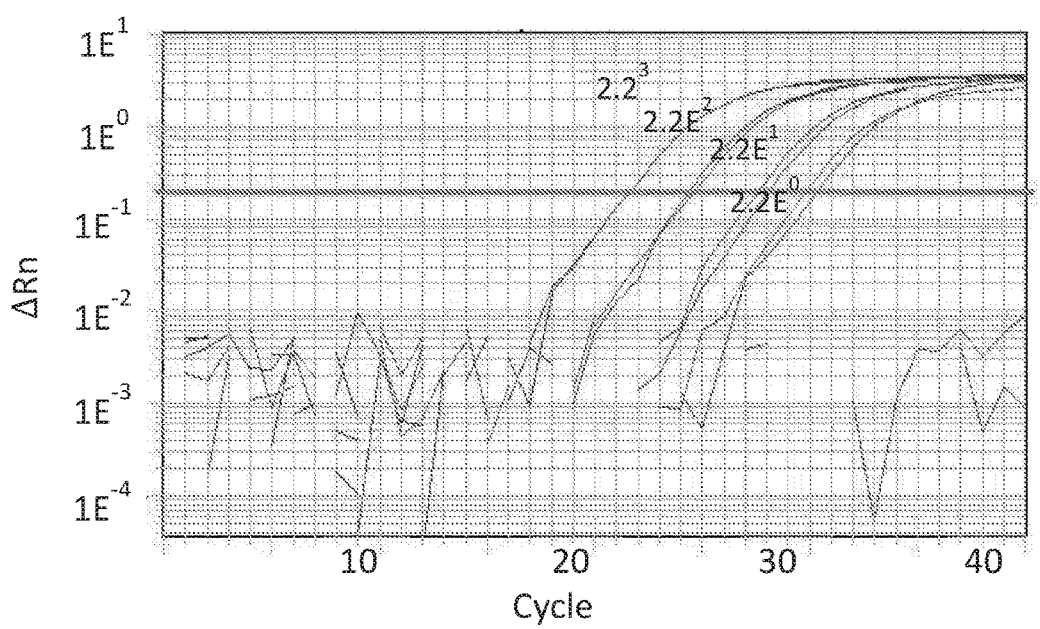
Figure 2A:
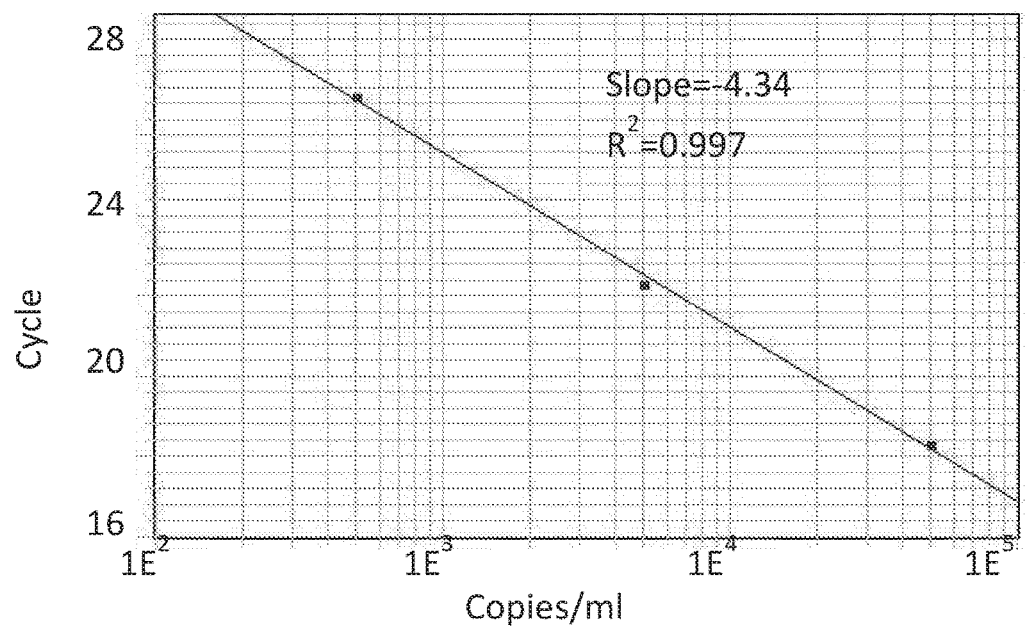
FIGS. 2A-2D. Internal Control pAW Test with the WHO International Standard of HIV-1 RNA (Version 3.0) and VQA control showing graphs of 2E4 internal control pAW used in every sample to validate quality of RNA extraction used in HIV-1 Ultra PCR Assay with Primer and Probe Set #1. All pAW RNA standards and unknown samples were tested in singlet.
Figure 2B:
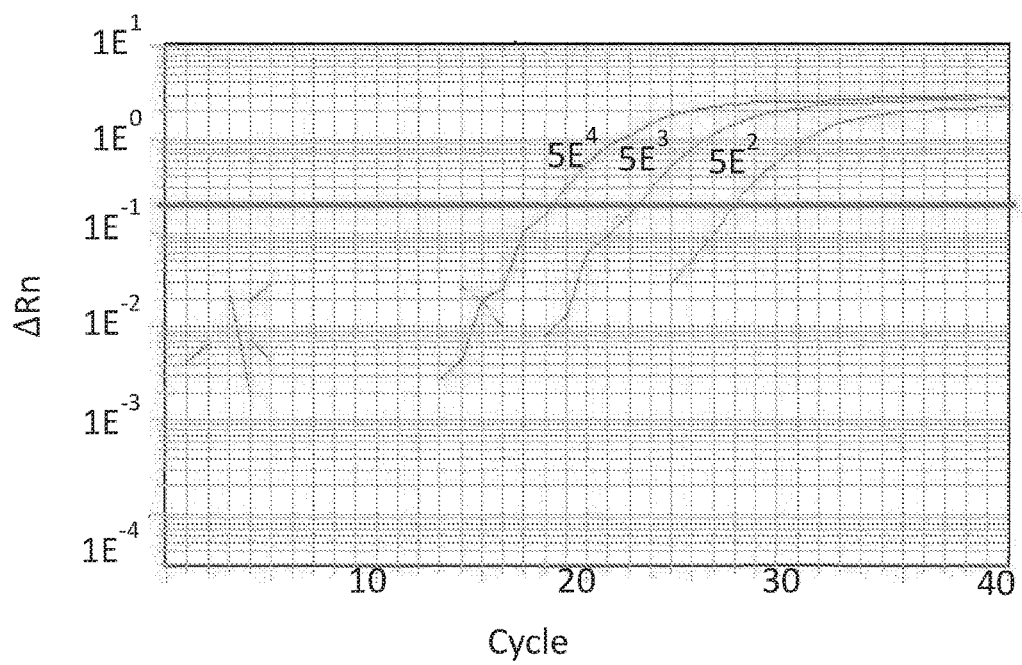
Figure 2C:
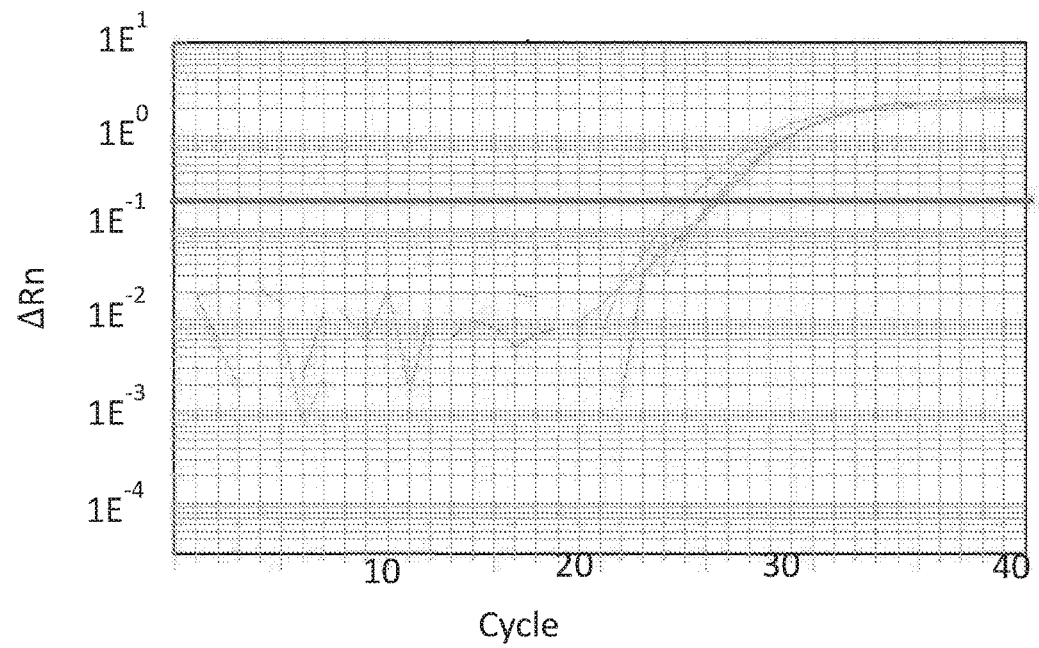
Figure 2D:
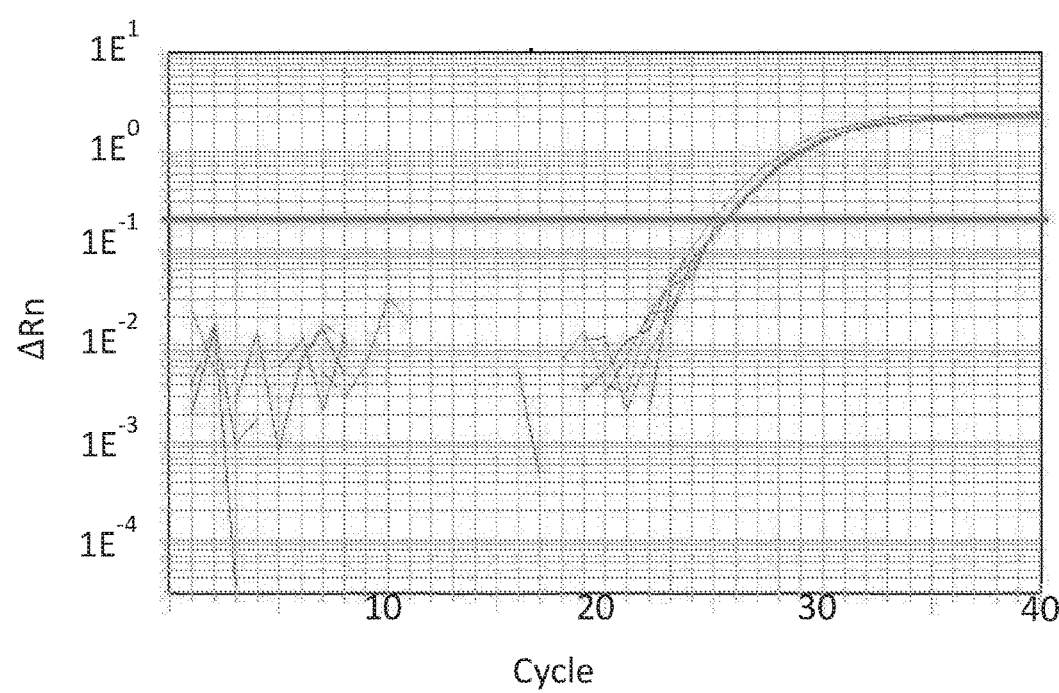
Figure 3A:
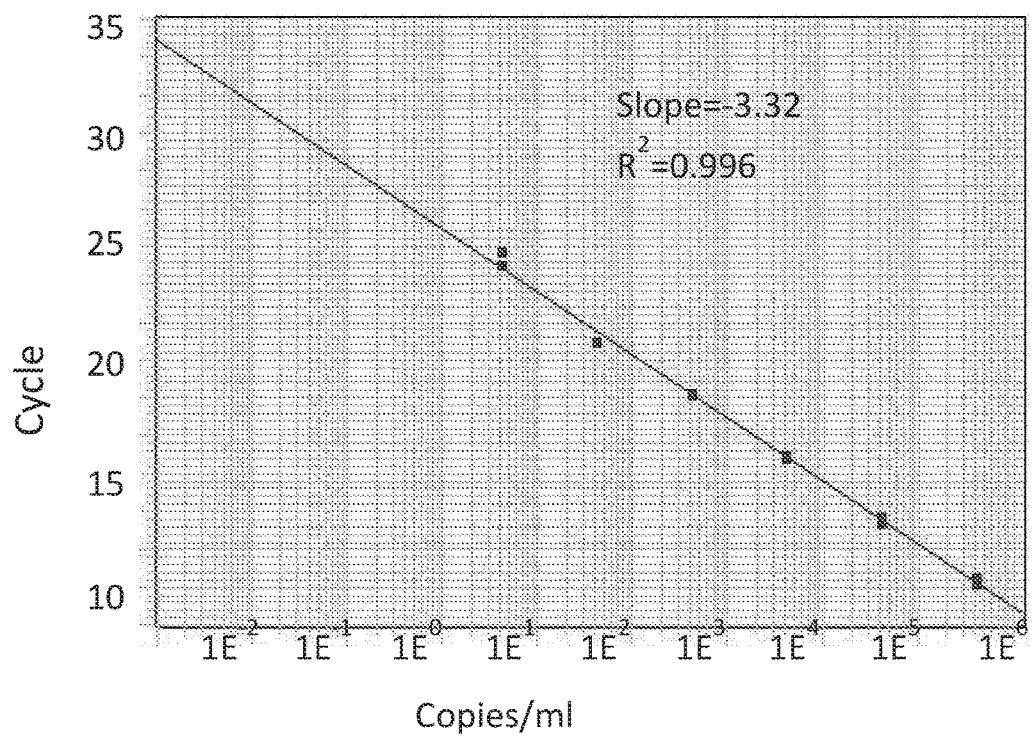
FIGS. 3A-3D. Detection of the WHO International Standard by HIV-1 Ultra PCR with Primer and Probe Set #2. FIG. As described in FIG. 1.
Figure 3B:
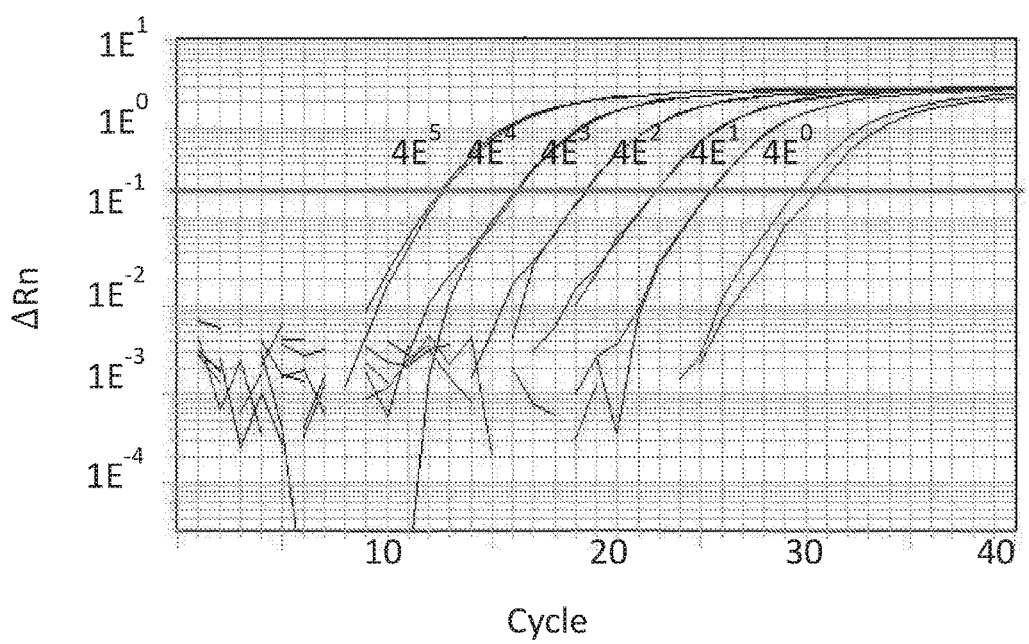
Figure 3C:
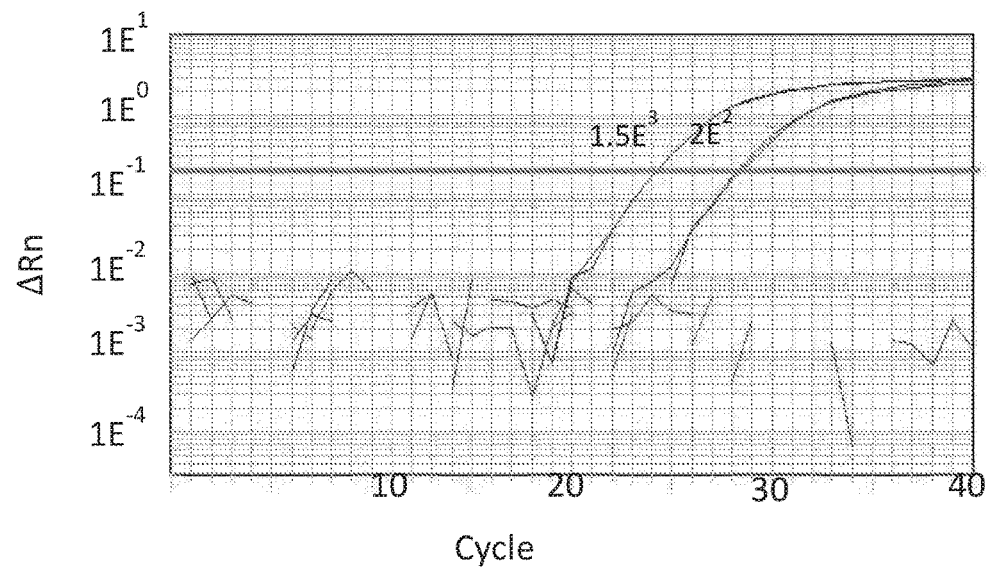
Figure 3D:
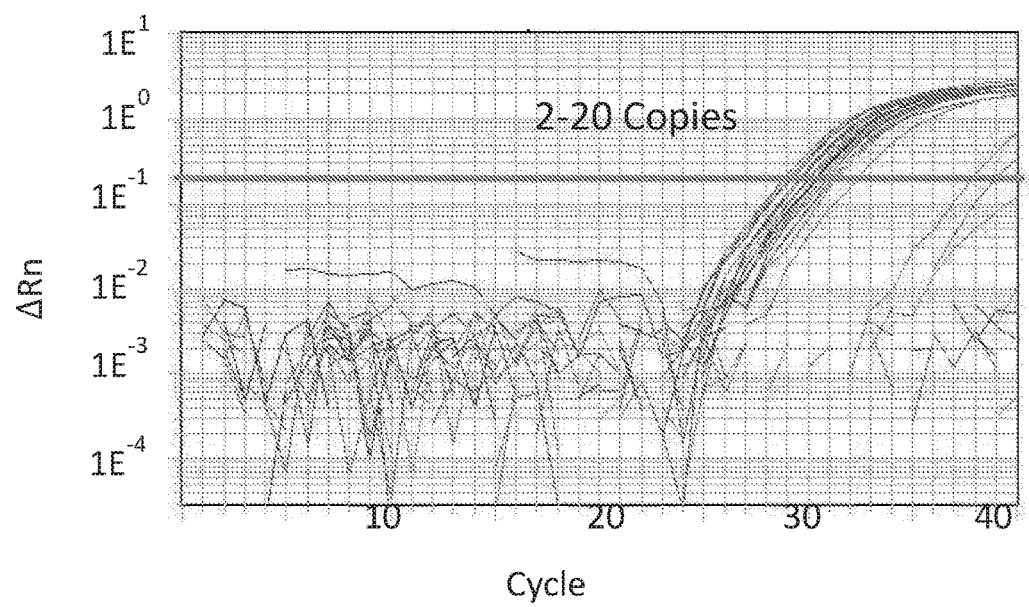
Figure 4A:
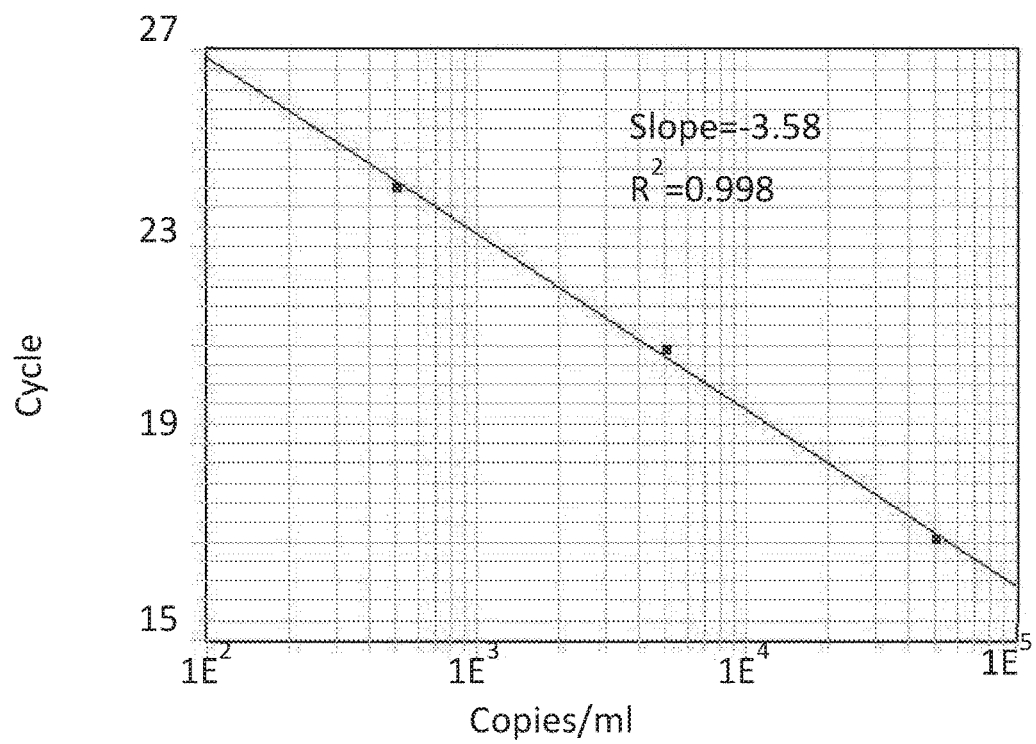
FIGS. 4A-4D. Internal Control pAW Test with the WHO International Standard of HIV-1 RNA (Version 3.0) and VQA control showing graphs of 2E4 internal control pAW used in every sample to validate quality of RNA extraction used in HIV-1 Ultra PCR Assay with Primer and Probe Set #2. All pAW RNA standards and unknown samples were tested in singlet. As described in FIG. 2.
Figure 4B:
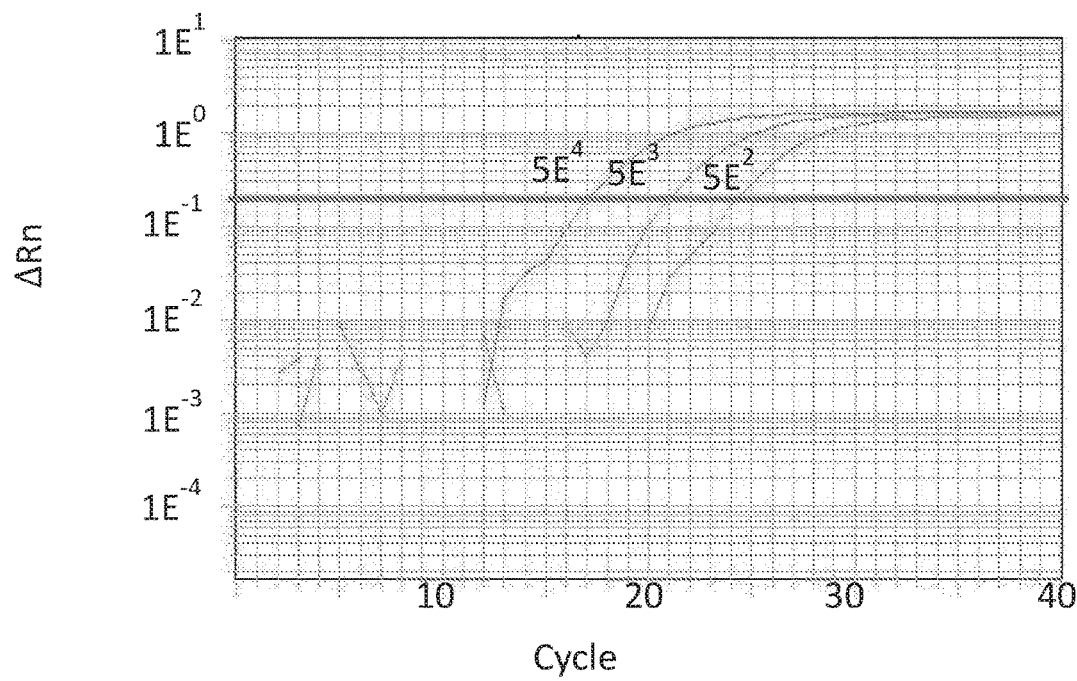
Figure 4C:
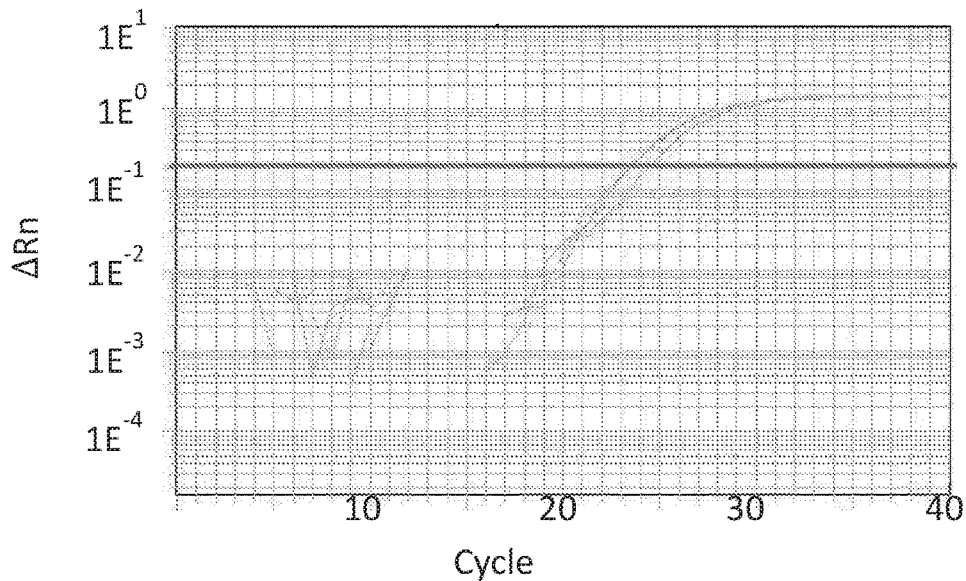
Figure 4D:
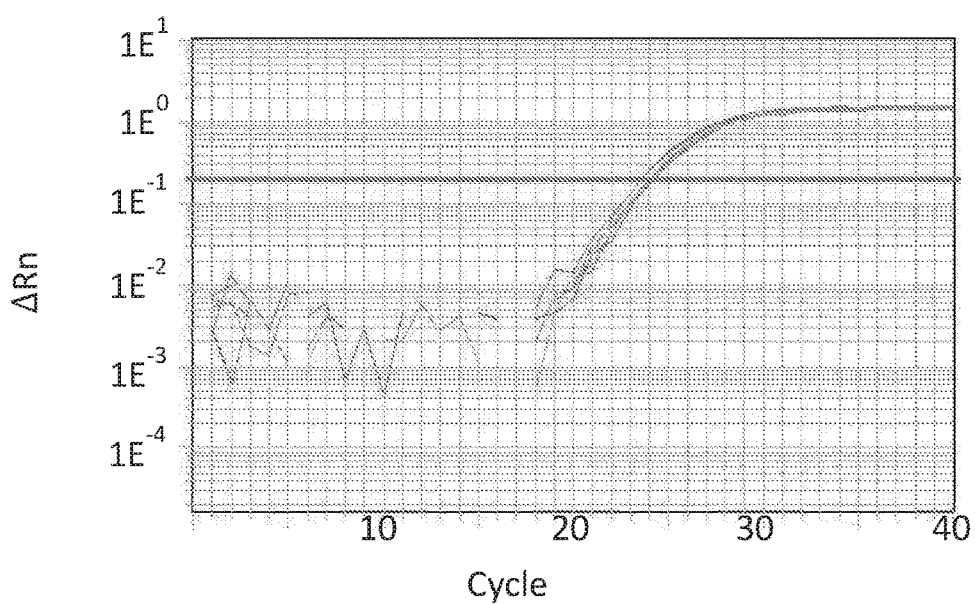
Figure 5A:
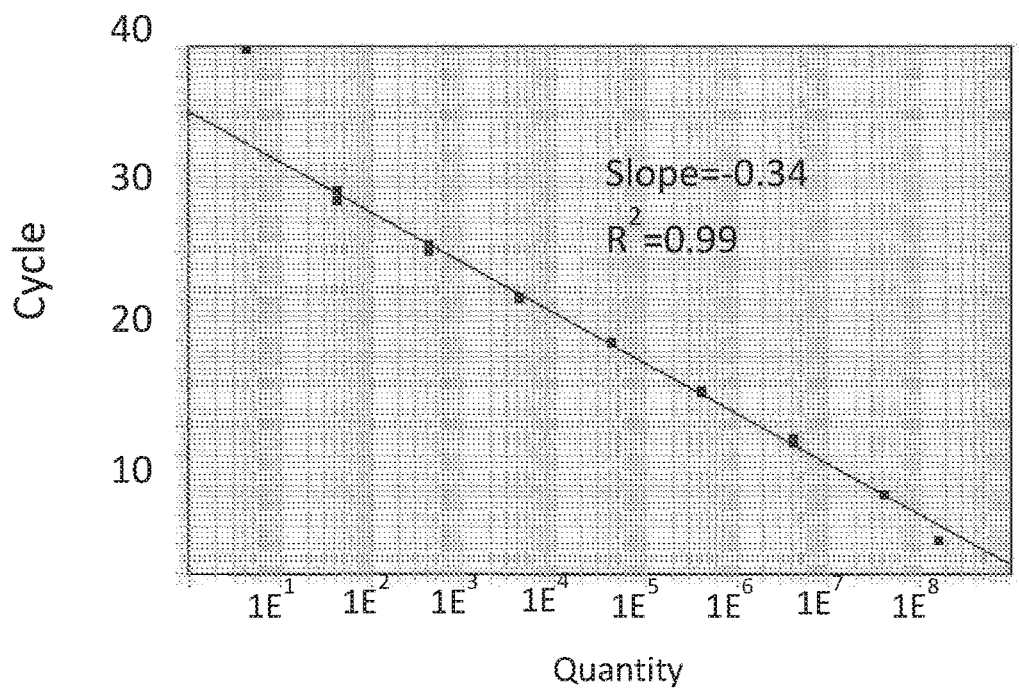
FIGS. 5A-5C. Detection of The AcroMetrix@HCV Standard with HCV Ultra PCR with HCV Primer and Probe set #1.
Figure 5B:
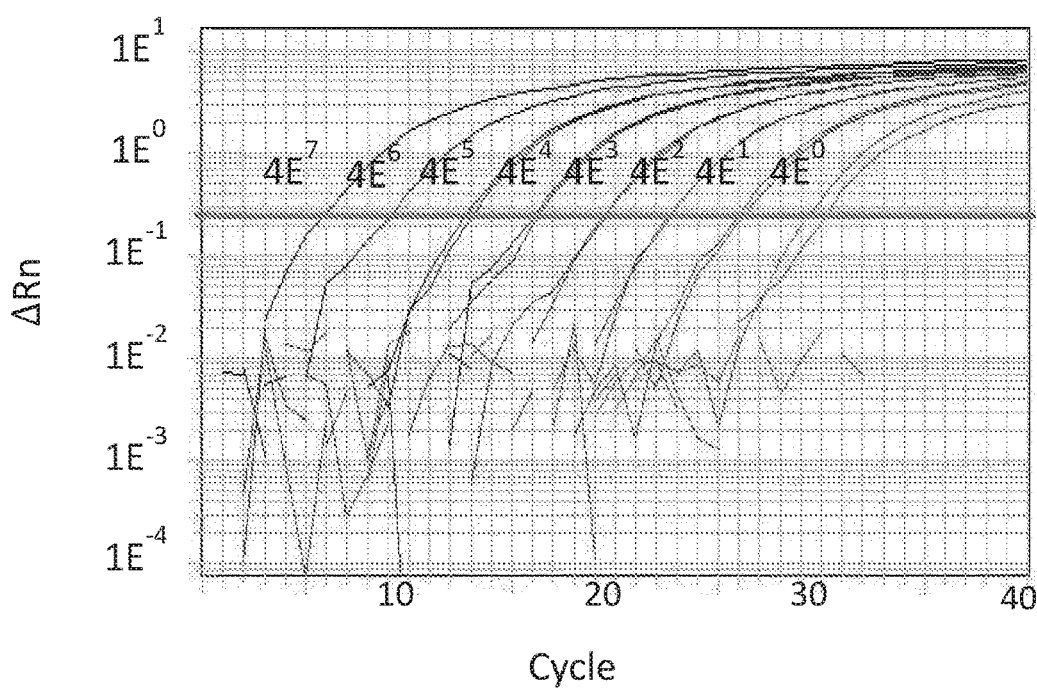
Figure 5C:
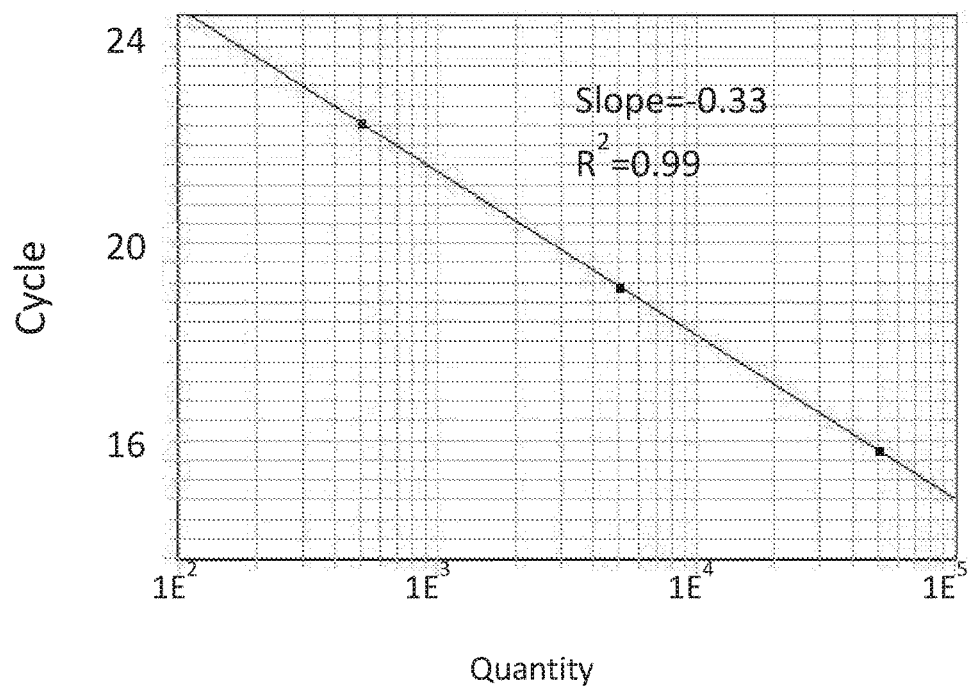
Figure 5D:
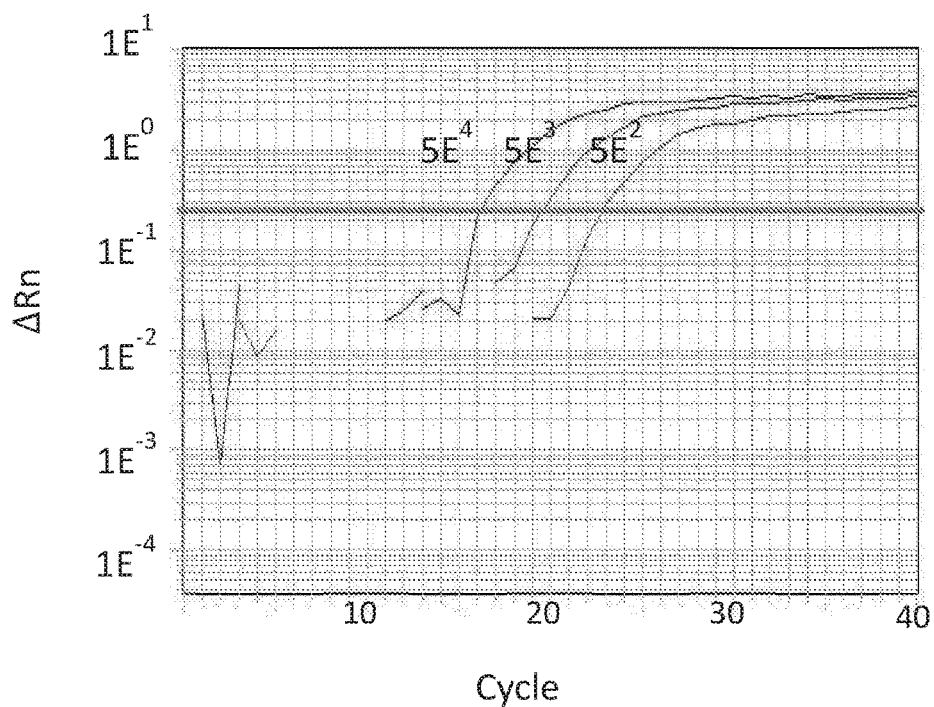
FIG. 5D is an Amplification plot showing amplification curves of pAW standards. Cycle threshold sets at 0.2 indicated by the thick horizontal line. The cycle number (Ct) value for each pAW standard used to determine the line in FIG. 5C.
Figure 6A:
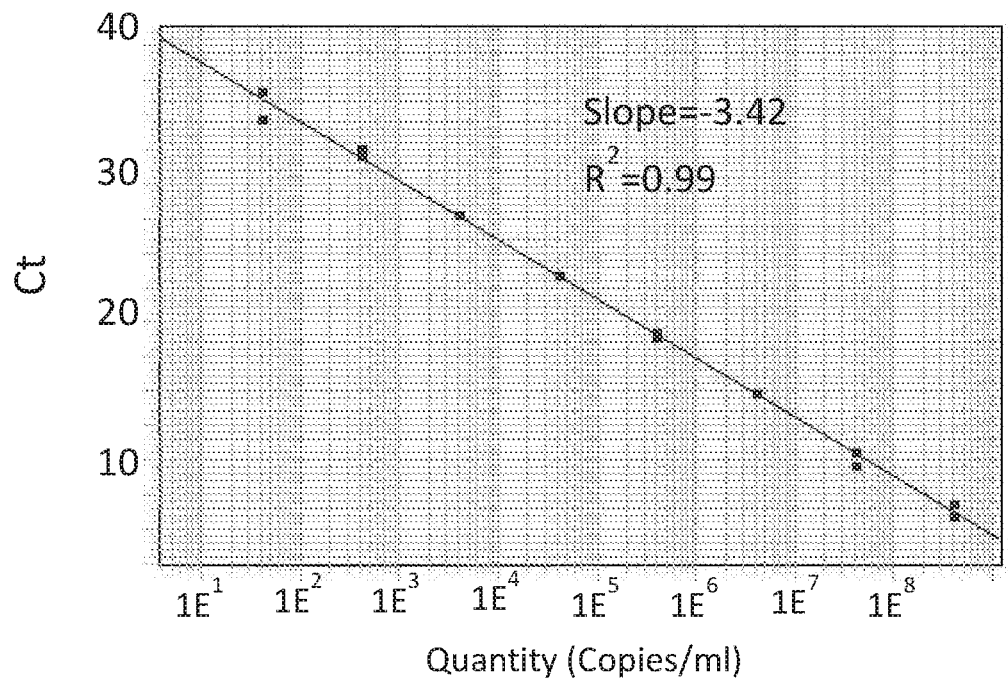
FIGS. 6A-6D. Detection of the AcroMetrix@HCV Standard with HCV Ultra PCR with HCV Primer and Probe Set #2.
Figure 6B:
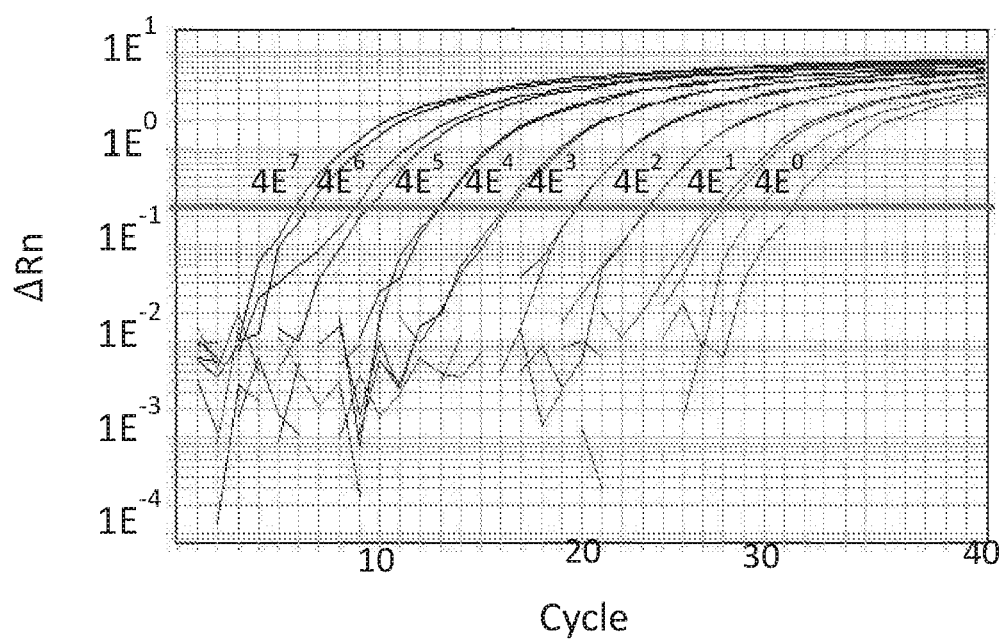
Figure 6C:
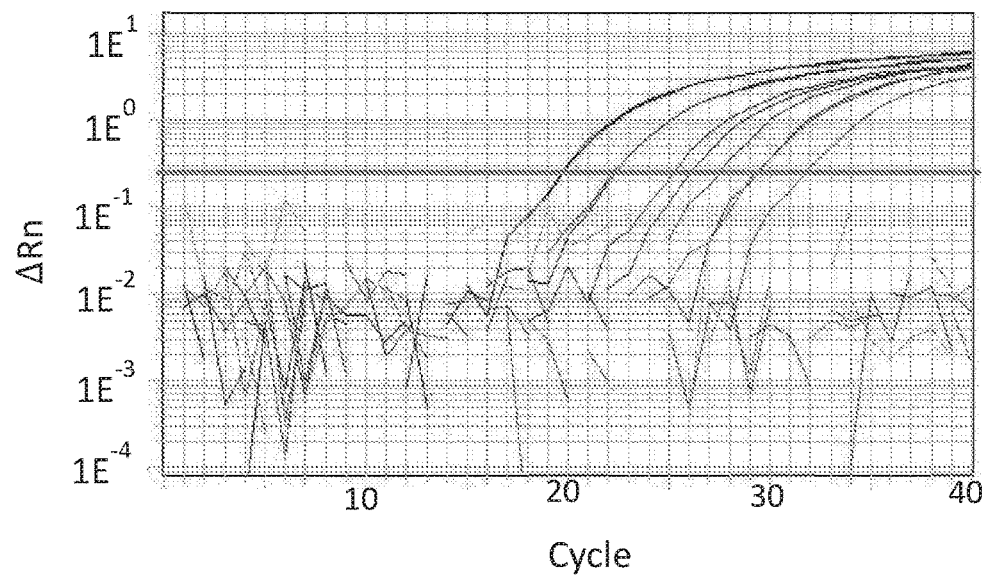
Figure 6D:
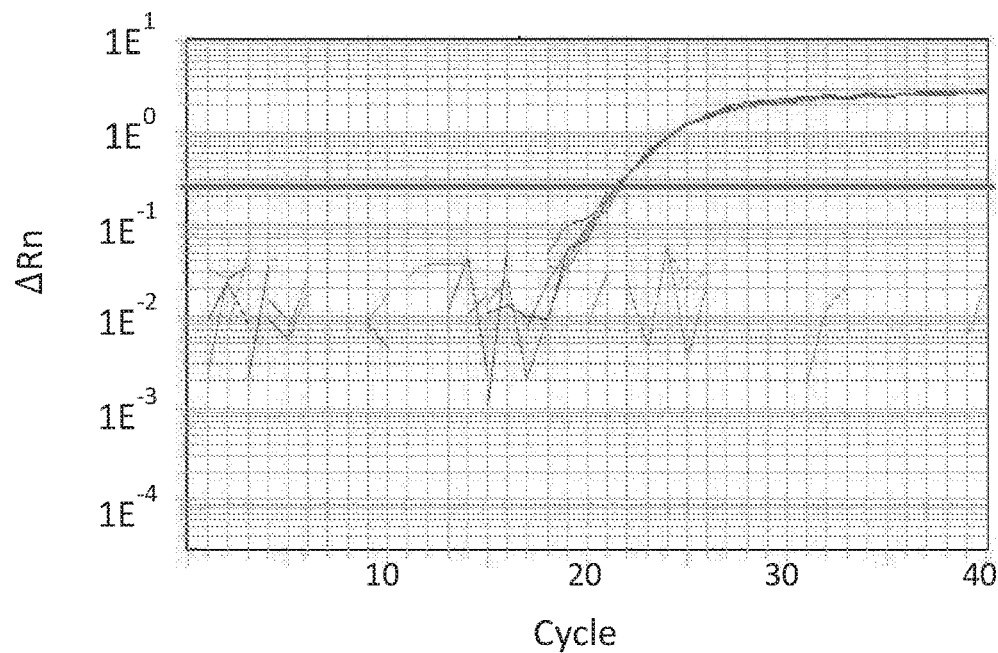

A nucleotide acid sequence alignment was set up that contained HIV-1 sequences present in GenBank and the Los Alamos National Laboratory database (HIV-1 2012). Primers and probe binding in conserved domains were designed by analyses of sequences including alignment and further justified by the Primer Express software (Life Technologies) and related salted and unsalted buffer conditions. The primers and probes in Table 1 were designed for the detection of all subtypes of HIV-1 M group and most of 0 group, while primers and probes in Table 2 were designed for all HCV subtypes. Three pairs of primers were designed for triple rounds of PCR for each Ultra PCR. The first round PCR is designed for high specificity with primer pair designed with higher annealing temperature (65-71° C.). The second round PCR remains more specificity with primers at relatively high annealing temperature (60-64° C.) and increased amplification efficiency. The third round PCR is designed for the maximal amplification of the first and second rounds of PCR products with primers at low annealing temperature (50-55° C.). So, the combination of the first, second and third rounds of PCR significantly improve the sensitivity and specificity of Ultra PCR (see FIGS. 1-6 and below). All the primers and probe for HIV-1 Ultra PCR (Table 1) and HCV Ultra PCR (Table 2) were synthesized from Life Technologies.

Example 2: Quantitation and Sensitivity of HIV-1 Detection

The WHO International Standard of HIV-1 RNA (version 3) was purchased from National Institute for Biological Standards and Control, Potters Bar, Hertfordshire, UK Official Medicines Control Laboratory. It has been assigned an International Unit value of 185,000 IU/ml (5.27 Log 10 IU/ml, 185,000 IU/ml=110,978 copies/mL). The WHO International Standard of HIV-1 RNA was serially diluted with HIV donor plasma (SaraCare Life Sciences) into 20, 10, 5, 4, 3, 2, 1 copies/mi. In addition to WHO International Standard, known quantity positive controls VQA 0, 200, 1500, 15000 copies/mi (Rush University Medical Center) and internal RNA extraction controls pAW 109 RNA (Life Technologies), ~1.2E4 copies/mi were used to extract RNA from each sample.

For HIV-1 RNA detection, the Ultra PCR was performed in 50 µl (final volume) of AgPath-ID™ one step RT-PCR reagents (Life Technologies), HIV-1 oligonucleotide primer and probe set #1 or set #2 including 5 nM of SEQ ID NOs: 1 and 2 (set #1) or SEQ ID NOs: 8 and 2 (set #2), 20 nM of SEQ ID NOs: 3 and 4 (set #1) or SEQ ID NOs: 9 and 10 (set #2), 0.5 µM of SEQ ID NOs: 5 and 6 (set #1) or SEQ ID NOs: 11 and 12 (set #2), and 0.4 µM of probes of set #1 or set #2 (Table 1); 10 µl of HIV-1 extracted RNA or DNA, 1×RT-PCR enzyme mix and 1 µl of RNase inhibitor (Life Technologies). To determine RNA extraction quality, a separate PCR reaction for each sample was used to quantify pAW amount. 5 µl of RNA was added to 20 ml of master mix for pAW quantification. The RT-PCR was performed as follows: reverse transcription at 45° C. for 10 min. and activation at 95° C. for 10 min followed by first round pre-amplification 5 cycles at 95° C. for 15 sec, 66° C. for 15 sec and 72° C. for 20 sec, 10 cycles at 95° C. for 15 sec, 63° C. for 15 sec and 72° C. for 20 sec and real time PCR for 40 cycles at 95° C. for 15 sec, 52° C. for 15 sec and 72° C. for 20 sec. HIV-1 RNA standard ranging from Negative, 4E0, 4E1, 4E2, 4E3, 4E4 and 4E5 copies with duplicates for each, internal control pAW109 RNA standard ranging from negative, 5e2, 5e3, 5e4 copies with in singlet, as well as diluted the WHO International Standard and VQAs in duplicate for each were included in each run. The detection limit experiments were repeated six times.

RT-PCR was carried out in 9700HP Real Time PCR Detection System from Life Technologies. Data were analyzed with Sequence Detection System (SDS) software 2.2.2 (7900HT, Applied Biosystems, Foster City, Calif.). The baseline was set up at threshold 0.20 for all detectors. The Ct values of unknown samples were plotted against quantification standard, and the number of HIV-1 RNA copies per ml was quantified. The criteria for an acceptable run are: no contamination, standard curve R2>=95%, duplicate within 2 Ct of each other, VQA within lot range and internal control pAW present at a range of 4000-20000 copies/ml.

The quantity of each sample was determined from the standard curve by the linear equation y=mx+b, where y is the log fluorescence ratio of the unknown sample, m is the slope of the standard curve (from log 1 to log 6), x is the log copies of HIV in the reaction, and b is the y-intercept of the standard curve (from log 1 to log 6). The quantity of pAW in each sample was determined by pAW standard curve ranging from log 2 to log 5.

The HIV RNA amplification curves and amplification plots, VQA amplification plots and the WHO International Standard detection, Internal control pAW amplification curves and amplification plots, as well as its amplification in each sample are shown in FIGS. 1-4. The summary data for the detection limit of Ultra PCR with the WHO International Standard of HIV-1 RNA is shown in Table 3. These data indicate that HIV-1 Ultra PCR can detect one HIV-1 RNA copy per assay, and can quantify HIV-1 RNA at 4 copies and higher, up to E8 HIV-1 RNA copies per ml plasma.

TABLE 3

Detection Rates of three sets of HIV-1 Ultra PCR (n = 50)

| HIV-1 RNA copies/assay | Primers/probe set #1 | Primers/probe set #2 |
|---|---|---|
| 10,000 | 100% | 100% |
| 1,000 | 100% | 100% |
| 100 | 100% | 100% |
| 10 | 100% | 100% |
| 5 | 100% | 100% |
| 4 | 100% | 100% |
| 3 | 98% | 100% |
| 2 | 92% | 90% |
| 1 | 60% | 66% |
| 0 | 0% | 0% |

Example 3: Quantitation and Sensitivity of HCV Detection

HCV Panel provides a standard across multiple test methods, enabling laboratories and manufacturers to assess the analytical performance of molecular test procedures (including the RNA extraction step) for the quantitative and qualitative determination of human hepatitis C virus (HCV) RNA.

This product can be used for training and proficiency testing of laboratory personnel, for lot-to-lot comparison of reagent test kits, and to evaluate and compare intralaboratory and interlaboratory assessments.

The AcroMetrix®HCV Panel members were produced by making quantitative dilutions of HCV RNA positive human source material into normal human plasma (NHP). The AcroMetrix®HCV Panel was designed and developed to meet the need for highly standardized and controlled nucleic acid testing of HCV. The panel helps to ensure that nucleic acid testing procedures for HCV RNA are properly validated, and that test results are consistent across manufacturers, testing laboratories, operators, platforms and assay formats. In order to meet global standardization and harmonization requirements, the panel has been calibrated against the World Health Organization (WHO) International Standard for HCV RNA.

Table 4, together with FIGS. 5 and 6, showed that HCV Ultra PCR can detect one HCV RNA copy per assay, and can quantify HCV RNA at 4 copies and higher, up to E8 HCV RNA copies per ml plasma.

TABLE 4

Detection Rates of two sets of HCV Ultra PCR (n = 50)

| HCV RNA copies/assay | Primers/probe set #1 | Primers/probe set #2 |
|---|---|---|
| 10,000 | 100% | 100% |
| 1,000 | 100% | 100% |
| 100 | 100% | 100% |
| 10 | 100% | 100% |
| 5 | 100% | 100% |
| 4 | 100% | 100% |
| 3 | 98% | 96% |
| 2 | 82% | 80% |
| 1 | 52% | 56% |
| 0 | 0% | 0% |

Example 4: Quantitation of HIV-1 Subtypes

One of the challenges to detect HIV-1 is the genetic divergence of HIV-1 worldwide. It is important for an assay to be able to quantitatively and accurately detect all subtypes. Serum samples of twenty-three (23) HIV-1 isolates representing the major globally prevalent strains of subtypes A (2 isolates), B (5 isolates), C (4 isolates), D (1 isolate), E (7 isolates), F (3 isolates), and G (1 isolates) of HIV-1 Major (M) Group were obtained via the NIH AIDS Reagent Program at high concentrations determined by NIH VQA Program, and were 10-fold diluted into HIV-1 negative human plasma for HIV-1 RNA extraction. Both the Roche Cobas Taqman HIV-1 Monitor test and the HIV-1 Ultra PCR of the invention with Primers/probe set #1 and #2 were used to quantify simultaneously HIV-1 RNA copies in each of the 23 isolates from NIH, and the tests were repeated 6 times. The standard deviations (SD) of 0.08 to 0.21 $Log_{10}$ unit are shown with the Ultra PCR and are comparable with the Roche test SD (0.08 to 0.20 Logo unit). Comparative quantitation results with Roche and Ultra PCR with primers and probes #2 are summarized in Table 5. The $Log_{10}$ unit differences between the Roche and Ultra PCR are within −0.34 and 0.41. As reported, a difference of 0.5 $Log_{10}$ value is considered to be significant in the performance of viral RNA quantitation assays. No significant difference in HIV-1 RNA values between Roche and Ultra PCR was observed. These data indicate that HIV-1 Ultra PCR is capable of quantifying precisely a broad range of HIV-1 subtypes as compared to the Gold Standard Assay, Roche Taqman PCR.

TABLE 5

Quantification of HIV-1 Subtypes

| NIH Reagent Catalog # | Subtype | HIV-1 RNA $Log_{10}$ copies/ml by Roche test | HIV-1 RNA $Log_{10}$ copies/ml by Ultra PCR | $Log_{10}$ Difference of Roche − Ultra |
|---|---|---|---|---|
| 7683 | A | 8.65 | 8.82 | 0.17 |
| 7685 | A | 8.58 | 8.75 | 0.17 |
| 7686 | B | 8.46 | 8.68 | 0.22 |
| 7687 | B | 8.74 | 9.02 | 0.28 |
| 7689 | B | 9.00 | 9.18 | 0.18 |
| 7691 | B | 8.67 | 8.91 | 0.24 |
| 7692 | B | 8.70 | 8.55 | −0.15 |
| 7693 | C | 8.70 | 8.36 | −0.34 |
| 7694 | C | 9.00 | 9.22 | 0.22 |
| 7696 | C | 8.95 | 8.95 | 0.00 |
| 7697 | C | 8.89 | 8.90 | 0.01 |
| 7698 | D | 8.84 | 8.52 | −0.32 |
| 7701 | E | 8.71 | 8.70 | −0.01 |
| 7702 | E | 8.58 | 8.68 | 0.10 |
| 7703 | E | 8.30 | 8.19 | −0.11 |
| 7705 | E | 8.91 | 8.56 | −0.25 |
| 7706 | E | 8.67 | 8.46 | −0.21 |
| 7707 | E | 8.87 | 8.49 | −0.38 |
| 7708 | E | 8.81 | 8.55 | −0.27 |
| 7709 | F | 9.20 | 9.01 | −0.20 |
| 7710 | F | 8.60 | 9.01 | 0.41 |
| 7711 | F | 8.56 | 8.85 | 0.29 |
| 7712 | G | 8.85 | 8.55 | −0.30 |

Example 5: Detection of HIV-1 in Patient Samples

To further evaluate the performance and usage of Ultra PCR in clinics, 852 blood plasma samples from patients on HAART were tested by HIV-1 Ultra PCR and the Roche Cobas Taqman HIV-1 Monitor Test. Of the 752 plasma samples, 386 samples were collected at time points before patients started the HAART, 366 samples were collected at time points during 3-10 years HAART and were HIV-1 RNA negative by the Roche Cobas Taqman HIV-1 Monitor Test. The HIV-1 RNA copy numbers per ml of the 386 samples collected before HAART obtained from Ultra PCR are in good correlation with the copies obtained from the Roche HIV-1 Monitor Test, with R2 of 0.976 by Pearson's correlation coefficient. These data, together with Table 5 and FIGS. 1-4, indicate the accurate quantification of HIV-1 RNA by Ultra PCR.

In addition, 366 blood samples obtained after 3-10 year of HAART with undetected HIV-1 RNA by the Roche Cobas Taqman HIV-1 Monitor Test were further tested by Ultra PCR by both Primer/Probe set #1 and Primer/Probe set #2 with HIV-1 RNA detected in 188 samples (with Primer/Probe #1) and 182 samples (with Primer/Probe #2). Additionally, peripheral blood cells obtained at the same time points from the patients were tested by Ultra PCR for HIV-1 DNA with all HIV-1 DNA positive (range, 89-362 HIV-1 DNA copies/million cells). The results showed that 1) Ultra PCR with both primers/probe set #1 and 2 of the invention achieved higher sensitivity than the Roche assay; 2) both HIV-1 RNA and HIV DNA Ultra PCRs may be used to further monitor the viral reservoirs in patients on HAART, supporting use of Ultra PCR in evaluating the efficacy of anti-retroviral therapy.

TABLE 6

Detection of HIV-1 in HAART Patient Plasma (n = 366) undetected by Roche Cobas Taqman Monitor Test

| Methods | Positive Result | Negative Result |
|---|---|---|
| Ultra PCR with Primer/probe set #1 | 188 | 178 |
| Ultra PCR with Primer/probe set #2 | 182 | 184 |

REFERENCES

1. Douek, D. C., et al., *HIV preferentially infects HIV-specific CD4+ T cells*. Nature, 2002. 417(6884): p. 95-8.
2. *EASL International Consensus Conference on hepatitis C. Paris, 26-27 Feb. 1999. Consensus statement.* J Hepatol, 1999. 31 Suppl 1: p. 3-8.
3. *Recommendations for prevention and control of hepatitis C virus (HCV) infection and HCV-related chronic disease. Centers for Disease Control and Prevention.* MMWR Recomm Rep, 1998. 47(RR-19): p. 1-39.
4. Zhu, T., et al., *Persistence of Extraordinarily Low Levels of Genetic Homogeneous Human Immunodeficiency Virus type 1 in Exposed Seronegative Individuals*. J. Virol., 2003. 77(11): p. 6108-6116.
5. Zhu, T., et al., *Evidence for Human Immunodeficiency Virus Type 1 Replication In Vivo in CD14+ Monocytes and Its Potential Role as a Source of Virus in Patients on Highly Active Antiretroviral Therapy*. J. Virol., 2002. 76(2): p. 707-716.
6. O'Doherty, U., et al., *A sensitive, quantitative assay for human immunodeficiency virus type 1 integration*. J Virol, 2002. 76(21): p. 10942-50.
7. Yu, J. J., et al., *A more precise HIV integration assay designed to detect small differences finds lower levels of integrated DNA in HAART treated patients*. Virology, 2008. 379(1): p. 78-86.
8. Archin, N. M., et al., *Administration of vorinostat disrupts HIV-1 latency in patients on antiretroviral therapy*. Nature, 2012. 487(7408): p. 482-5.
9. Domadula, G., et al., *Residual HIV-1 RNA in blood plasma of patients taking suppressive highly active antiretroviral therapy*. JAMA, 1999. 282(17): p. 1627-32.
10. Espy, M. J., et al., *Real-time PCR in clinical microbiology: applications for routine laboratory testing*. Clin Microbiol Rev, 2006. 19(1): p. 165-256.
11. Chun, T. W., et al., *In vivo fate of HIV-1-infected T cells: Quantitative analysis of the transition to stable latency*. Nature Med., 1995. 1(12): p. 1284-1290.
12. Gulick, R. M., et al., *Treatment with indinavir, zidovudine, and lamivudine in adults with human immunodeficiency virus infection and prior antiretroviral therapy*. N. Engl. J. Med., 1997. 337(11): p. 734-739.
13. Hammer, S. M., et al., *A controlled trial of two nucleoside analogues plus indinavir in persons with human immunodeficiency virus infection and CD4 cell counts of 200 per cubic millimeter or less*. N Engl J Med, 1997. 337(11): p. 725-733.
14. Perelson, A. S., et al., *Decay characteristics of HIV-1-infected compartments during combination therapy*. Nature, 1997. 387: p. 188-191.
15. Chun, T. W., et al., *Quantification of latent tissue reservoirs and total body viral load in HIV-1 infection*. Nature, 1997. 387(6629): p. 183-8.
16. Finzi, D., et al., *Identification of a reservoir for HIV-1 in patients on highly active antiretroviral therapy*. Science, 1997. 278: p. 1295-1300.
17. Wong, J. K., et al., *Recovery of replication-competent HIV despite prolonged suppression of plasma viremia*. Science, 1997. 278: p. 1291-1300.
18. Hutter, G., et al., *Long-term control of HIV by CCR5 Delta32/Delta32 stem-cell transplantation*. N Engl J Med, 2009. 360(7): p. 692-8.
19. Dinoso, J. B., et al., *A comparison of viral loads between HIV-1-infected elite suppressors and individuals who receive suppressive highly active antiretroviral therapy*. Clin Infect Dis, 2008. 47(1): p. 102-4.
20. Graf, E. H., et al., *Elite suppressors harbor low levels of integrated HIV DNA and high levels of 2-LTR circular HIV DNA compared to HIV+ patients on and off HAART*. PLoS Pathog, 2011. 7(2): p. e1001300.
21. Chun, T. W., et al., *Presence of an inducible HIV-1 latent reservoir during highly active antiretroviral therapy*. Proc. Natl. Acad. Sci. USA, 1997. 94(24): p. 13193-7.
22. Finzi, D., et al., *Latent infection of CD4+ T cells provides a mechanism for lifelong persistence of HIV-1, even in patients on effective combination therapy*. Nat. Med., 1999. 5(5): p. 512-7.
23. Siliciano, J. D., et al., *Long-term follow-up studies confirm the stability of the latent reservoir for HIV-1 in resting CD4+ T cells*. Nat Med, 2003. 9(6): p. 727-8.
24. Chun, T. W., et al., *Relationship between pre-existing viral reservoirs and the re-emergence of plasma viremia after discontinuation of highly active anti-retroviral therapy*[see comments]. Nat Med, 2000. 6(7): p. 757-61.
25. Davey, R. T., Jr., et al., *HIV-1 and T cell dynamics after interruption of highly active antiretroviral therapy (HAART) in patients with a history of sustained viral suppression*. Proc Natl Acad Sci USA, 1999. 96(26): p. 15109-14.
26. Richman, D. D., at al., *The challenge of finding a cure for HIV infection*. Science, 2009. 323(5919): p. 1304-7.
27. Dinoso, J. B., et al., *Treatment intensification does not reduce residual HIV-1 viremia in patients on highly active antiretroviral therapy*. Proc Natl Acad Sci USA, 2009. 106(23): p. 9403-8.
28. Deeks, S. G., et al., *Towards an HIV cure: a global scientific strategy*. Nat Rev Immunol, 2012. 12(8): p. 607-14.

29. Fried, M. W., et al., *Peginterferon alfa-2a plus ribavirin for chronic hepatitis C virus infection.* N Engi J Med, 2002. 347(13): p. 975-82.
30. Makiyama, A., et al., *Characteristics of patients with chronic hepatitis C who develop hepatocellular carcinoma after a sustained response to interferon therapy.* Cancer, 2004. 101(7): p. 1616-22.
31. Kobayashi, S., at al., *Development of hepatocellular carcinoma in patients with chronic hepatitis C who had a sustained virological response to interferon therapy: a multicenter, retrospective cohort study of 1124 patients.* Liver Int, 2007. 27(2): p. 186-91.
32. Scherzer, T. M., et al., *Hepatocellular carcinoma in long-term sustained virological responders following antiviral combination therapy for chronic hepatitis C.* J Viral Hepat, 2008. 15(9): p. 659-65.
33. Sewell, J. L., K. M. Stick, and A. Monto, *Hepatocellular carcinoma after sustained virologic response in hepatitis C patients without cirrhosis on a pretreatment liver biopsy.* Eur J Gastroenterol Hepatol, 2009. 21(2): p. 225-9.
34. Morgan, T. R., et al., *Outcome of sustained virological responders with histologically advanced chronic hepatitis C.* Hepatology, 2010. 52(3): p. 833-44.
35. van der Meer, A. J., et al., *Association between sustained virological response and all-cause mortality among patients with chronic hepatitis C and advanced hepatic fibrosis.* JAMA, 2012. 308(24): p. 2584-93.
36. Sulkowski, M. S., et al., *Daclatasvir plus sofosbuvir for previously treated or untreated chronic HCV infection.* N Engl J Med, 2014. 370(3): p. 211-21.
37. Fiebig, E. W., et al., *Dynamics of HIV viremia and antibody seroconversion in plasma donors: implications for diagnosis and staging of primary HIV infection.* AIDS, 2003. 17(13): p. 1871-9.
38. Saez-Cirion, A., et al., *Post-treatment HIV-1 controllers with a long-term virological remission after the interruption of early initiated antiretroviral therapy ANRS VISCONTI Study.* PLoS Pathog, 2013. 9(3): p. e1003211.
39. Lok, A. S. and B. J. McMahon, *Chronic hepatitis B.* Hepatology, 2007. 45(2): p. 507-39.
40. Iloeje, U. H., et al., *Risk and predictors of mortality associated with chronic hepatitis B infection.* Clin Gastroenterol Hepatol, 2007. 5(8): p. 921-31.
41. Alter, M. J., et al., *The prevalence of hepatitis C virus infection in the United States, 1988 through 1994.* N Engl J Med, 1999. 341(8): p. 556-62.
42. Jaeckel, E., et al., *Treatment of acute hepatitis C with interferon alfa-2b.* N Engl J Med, 2001. 345(20): p. 1452-7.

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for detecting HCV in a sample comprising: isolating RNA in a sample, submitting the isolated RNA to reverse transcription PCR, contacting the resulting reverse transcription PCR product with a set of primers, and submitting the resulting mixture to one or more nucleic acid amplification reactions, wherein the set of primers comprises the collection of oligonucleotides comprising: one or more forward primers selected from the group consisting of SEQ ID NO:16, SEQ ID NO:18, SEQ ID NO:20, complementary sequences thereof, active fragments thereof, and combinations thereof; one or more reverse primers selected from the group consisting of SEQ ID NO:17, SEQ ID NO:19, SEQ ID NO:21, SEQ ID NO:23, SEQ ID NO:24, SEQ ID NO:27, SEQ ID NO:28, SEQ ID NO:29, SEQ ID NO:30, complementary sequences thereof, active fragments thereof, and combinations thereof; and one or more probes selected from the group consisting of SEQ ID NO:22, SEQ ID NO:25, SEQ ID NO:26, complementary sequences thereof, active fragments thereof, and combinations thereof.

2. A method for detecting HCV in a sample comprising: isolating RNA in a sample, submitting the isolated RNA to reverse transcription PCR, contacting the resulting reverse transcription PCR product with a set of outer primers, and submitting the resulting mixture to a first nucleic acid amplification reaction, wherein the primers comprise a combination of oligonucleotides comprising an outer, middle and inner set of primers wherein the outer primers comprise SEQ ID NO:16, SEQ ID NO:17 or active fragments thereof; the middle primers comprise SEQ ID NO:18, SEQ ID NO: 19 or active fragments thereof; the inner primers comprise SEQ ID NO:20, SEQ ID NO:21 or active fragments thereof.

3. The method of claim 2, further comprising contacting a product from the first nucleic acid amplification reaction with a set of middle primers and submitting the resulting mixture to a second nucleic acid amplification reaction.

4. The method of claim 3, further comprising contacting a product from the second nucleic acid amplification reaction with a set of inner primers and submitting the resulting mixture to a third nucleic acid amplification reaction.

5. The method of claim 4, further comprising contacting a product from the third nucleic amplification reaction with a probe for quantitation by real time PCR; wherein the probe is selected from the group consisting of SEQ ID NO:22, or active fragments thereof.

6. A method for detecting HCV in a sample comprising: isolating RNA in a sample, submitting the isolated RNA to reverse transcription PCR, contacting the resulting reverse transcription PCR product with a set of outer primers, and submitting the resulting mixture to a first nucleic acid amplification reaction, wherein the primers comprises a combination of oligonucleotides comprising an outer, middle and inner set of primers wherein the outer primers comprise SEQ ID NO:16, SEQ ID NO:23 or active fragments thereof; the middle primers comprise SEQ ID NO:18, SEQ ID NO:24 or active fragments thereof; the inner primers comprise SEQ ID NO:20, SEQ ID NO:21 or active fragments thereof.

7. The method of claim 6, further comprising contacting a product from the first nucleic acid amplification reaction with a set of middle primers and submitting the resulting mixture to a second nucleic acid amplification reaction.

8. The method of claim 7, further comprising contacting a product from the second nucleic acid amplification reaction with a set of inner primers and submitting the resulting mixture to a third nucleic acid amplification reaction.

9. The method of claim 8, further comprising contacting a product from the third nucleic amplification reaction with the probe for quantitation by real time PCR; wherein the probe is selected from the group consisting of: SEQ ID NO:25, SEQ ID NO:26, and active fragments thereof.

10. The method of claim 4, wherein the first nucleic acid amplification reaction is performed at a temperature of about 65-71° C., the second nucleic acid amplification reaction is performed at a temperature of about 60-64° C., and the third nucleic acid amplification reaction is performed at a temperature of about 50-55° C.

11. The method of claim 4, wherein the method is carried out in a single tube.

12. The method of claim 1, wherein the sample contains less than 5 copies of the RNA virus.

13. A method for monitoring the efficacy of anti-retroviral treatment in a subject infected with HCV, the method comprising:

(a) subjecting a sample obtained from the subject to the method of claim 8; and
(b) determining whether the sample contains fewer copies of the virus per milliliter than a predetermined threshold;
wherein a reduction in copies of the virus per milliliter sample is indicative of effective anti-retroviral treatment.

14. The method of claim 13, wherein the predetermined threshold is an amount detected in a prior sample obtained from the subject at a previous time point.

15. The method of claim 13, wherein the predetermined threshold is 5 copies of virus per milliliter sample.

16. A method for detecting acute early HCV infection in a subject, the method comprising:

(a) subjecting a sample obtained from the subject to the method of claim 1; and
(b) determining whether the sample contains a detectable amount of HCV RNA;
wherein the presence of a detectable amount of HCV RNA is indicative of acute early HCV infection.

17. The method of claim 16, wherein the sample is blood, plasma, serum, saliva, urine, cerebral spinal fluid, milk, cervical secretions, semen, tissue, or cell cultures.

18. The method of claim 1, wherein the one or more forward primers comprise SEQ ID NO:16, SEQ ID NO:18, SEQ ID NO:20, or active fragments thereof; and the one or more reverse primers comprise SEQ ID NO:17, SEQ ID NO:19, SEQ ID NO:21, or active fragments thereof; and the probe comprises SEQ ID NO:22, or an active fragment thereof.

19. The method of claim 18, wherein the set of primers comprises an outer, middle and inner set of primers, wherein the outer primers comprise SEQ ID NO:16, SEQ ID NO:17 or active fragments thereof; the middle primers comprise SEQ ID NO:18, SEQ ID NO: 19 or active fragments thereof; the inner primers comprise SEQ ID NO:20, SEQ ID NO:21 or active fragments thereof; and the one or more probes selected from the group consisting of SEQ ID NO:22, or active fragments thereof.

20. The method of claim 1, wherein the one or more forward primers comprise SEQ ID NO:16, SEQ ID NO: 18, SEQ ID NO:20, or active fragments thereof; and the one or more reverse primers comprise SEQ ID NO:23, SEQ ID NO:24, SEQ ID NO:21, or active fragments thereof; and the one or more probes comprise SEQ ID NO:25, SEQ ID NO:26, or active fragments thereof.

21. The method of claim 1, wherein the collection of oligonucleotides comprises an outer, middle and inner set of primers wherein the outer primers comprise SEQ ID NO:16, SEQ ID NO:23 or active fragments thereof; the middle primers comprise SEQ ID NO:18, SEQ ID NO:24 or active fragments thereof; the inner primers comprise SEQ ID NO:20, SEQ ID NO:21 or active fragments thereof; and one or more probes comprise SEQ ID NO:25, SEQ ID NO:26, or active fragments thereof.

22. The method of claim 8, wherein the first nucleic acid amplification reaction is performed at a temperature of about 65-71° C., the second nucleic acid amplification reaction is performed at a temperature of about 60-64° C., and the third nucleic acid amplification reaction is performed at a temperature of about 50-55° C.

23. The method of claim 8, wherein the method is carried out in a single tube.

24. The method of claim 4, wherein the sample contains less than 5 copies of the RNA virus.

25. The method of claim 8, wherein the sample contains less than 5 copies of the RNA virus.

\* \* \* \* \*